United States Patent [19]
Raben et al.

[11] Patent Number: 5,484,703
[45] Date of Patent: Jan. 16, 1996

[54] ASSAY USING RECOMBINANT HISTIDYL-TRNA SYNTHETASE

[75] Inventors: Nina Raben, Rockville; Ralph Nichols, Columbia, both of Md.; Paul Plotz, Washington, D.C.; Richard Leff, Charleston, S.C.

[73] Assignee: United States of America, Washington, D.C.

[21] Appl. No.: 52,404

[22] Filed: Apr. 22, 1993

[51] Int. Cl.$^6$ ................................................. G01N 33/564
[52] U.S. Cl. ........................ 435/7.4; 435/7.1; 435/975; 436/506; 436/811
[58] Field of Search .......................... 435/7.1, 7.4, 975; 436/506, 811

[56] References Cited

PUBLICATIONS

Luckow et al., Trends in the development of baculovirus expression vectors, Biotechnology 6: 47–55, 1988.
Raben et al., Expression of recombinant human histidyl tRNA Synthetase, an autoantigen, in baculovirus–transfected insect cells, Arthritis and Rheumatism 35 (9): S170, 1992.
Biswas, et al., "Stimulation and Partial Stabilization of Human Histidyl–tRNA Synthetase by Hemoglobin" Feb. 229(1): 203–205 (1988).
Biswas, et al., "An Efficient Method for Enrichment of Histidyl–tRNA Synthetase from HeLa Cells" J. of Immunological Methods 98: 235–241 (1987).
Cusack, et al., "Sequence, Structural and Evolutionary Relationships Between Class 2 Aminoacyl–tRNA Synthetases" Nucl. Acids Res. 19(13): 3489–3498 (1991).
Eriani, et al., "Partition of tRNA Synthetases into Two Classes Based on Mutually Exclusive Sets of Sequence Motifs" Nature 347: 203–206 (1990).
Fett, et al., "The Primary Structure of Human Glutaminyl–tRNA Synthetase" J. of Biol. Chem. 266(3): 1448–1455 (1991).
Garret, et al., "A Mammalian Tryptophanyl–tRNA Synthetase Shows Little Homology to Prokaryotic Synthetases but Near Identity with Mammalian Peptide Chain Release Factor" Biochelmistry 30: 7809–7817 (1991).
Love, et al., "A New Approach to the Classification of Idiopathic Inflammatory Myopathy: Myositis–Specific Autoantibodies Define Useful Homogeneous Patient Groups" Medicine 70(6): 360–373 (1991).
Miller, et al., "The Role of an Autoantigen, Histidyl–tRNA Synthetase, in the Induction and Maintenance of Autoimmunity" Proc. Natl. Acad. Sci. 87: 9933–9937 (1990).
Jacobo—Molina, et al., "cDNA Sequence, Predicted Primary Structure, and Evolving Amphiphilic Helix of Human Aspartyl–tRNA Synthetase" J. of Biol. Chem. 264(28): 16608–16612 (1989).
Natsoulis, et al., "The HTS1 Gene Encodes Both the Cytoplasmic and Mitochondrial Histidine tRNA Synthetases of S. cerevisiae" Cell 46: 235–243 (1986).

Raben, et al., "Human Histidyl–tRNA Synthetase: Recognition of Amino Acid Signature Regions in Class 2a Aminoacyl–tRNA Synthetases" Nucl. Acids Res. 20(5): 1075–1081 (1992).
Ramsden, et al., "Epitope Mapping of the Cloned Human Autoantigen, Histidyl–tRNA Synthetase" J. of Immunology 143(7): 2267–2272 (1989).
Ruff, et al., "Class II Aminoacyl Transfer RNA Synthetases: Crystal Structure of Yeast Aspartyl–tRNA Synthetase Complexed with tRNA$^{Asp}$" Science 252: 1682–1689 (1991).
Targoff, et al., "Measurement of Antibody to Jo–1 by Elisa and Comparison to Enzyme Inhibitory Activity" J. of Immunology 138(9): 2874–2882 (1987).
Tsui, et al., "Mapping the Epitopes on Jo–1 (Histidyl–tRNA Synthetase)" Arthritis & Rheumatism 31(4 Suppl): B35 (1988).
Tsui, et al., "Amplification of the Gene for Histidyl–tRNA Synthetase in Histidinol–Resistant Chinese Hamster Ovary Cells" Mol. and Cell. Biol. 5(9): 2381–2388 (1985).
Tsui, et al., "Isolation, Structure and Expression of Mammalian Genes for Histidyl–tRNA Synthetase" Nucl. Acids Res. 15(8): 3349–3367 (1987).
Tsui, et al., "Structural Analysis of the 5' Region of the Chromosomal Gene for Hamster Histidyl–tRNA Synthetase" Gene: 61: 349–361 (1987).
Eisenbeis, et al., "The Nucleotide Sequence of the Promoter Region of hisS, the Structural Gene for Histidyl–tRNA Synthetase" Gene 18: 107–114 (1982).
Farhoum, et al., "Purification of Mammalian Histidyl–tRNA Synthetase and Its Interaction with Myositis–Specific Anti Jo–1 Antibodies" Biochemistry 26: 5871–5877 (1987).
Kontis, et al., "Isolation of a cDNA Clone for Human Threonyl–tRNA Synthetase Amplification of the Structural Gene in Borrelidin–Resistant Cell Lines" Mol. and Cell. Biol. 9(5): 1832–1838 (1989).
Raben, et al., "The Correct Sequence of Human Histidyl–tRNA Synthetase, an Important Autoantigen" J. of Cell Biol. (3 Part 2): 89a (1991).
Walker, et al., "Improved Detection of Anti–Jo–1 Antibody, a Marker for Myositis, Using Purified Histidyl–tRNA Synthetase" J. of Immunological Methods 96: 149–156 (1987).
Walker, et al., "Purification of Bovine Liver Histidyl–tRNA Synthetase, the Jo–1 Antigen of Polymyositis" Biol. Chem. Hoppe Seyler 368(5): 531–537 (1987).
Yoshida, et al., "The Precipitating Antibody to an Acidic Nuclear Protein Antigen, the Jo–1, in Connective Tissue Diseases" Arthritis & Rheumatism 26(5): 604–611 (1983).
Freedman, et al., J. Biol. Chem. 260: 10063–10068 (1985).
Nishikai, et al., Arthritis Rheum. 23: 881–888 (1980).

*Primary Examiner*—Toni R. Scheiner
*Assistant Examiner*—Donna C. Wortman
*Attorney, Agent, or Firm*—Knobbe, Martens, Olson & Bear

[57] ABSTRACT

Recombinant Histidyl tRNA synthetase produced by non-mammalian host cells is used in a sensitive assay to determine the presence of autoimmune diseases in mammals. Methods for isolating, cloning and expressing rHRS are described. In addition, a kit for determining the presence of an autoimmune disease is provided.

10 Claims, 5 Drawing Sheets

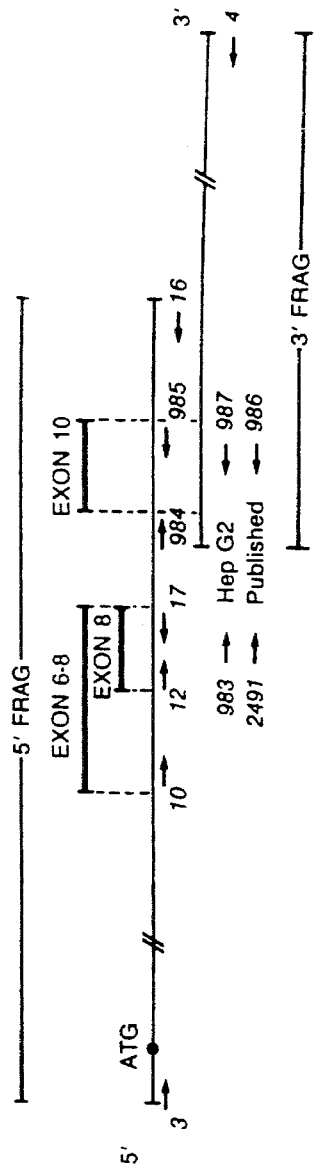
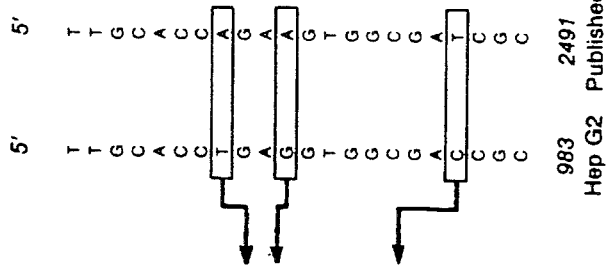
FIG. 1A
FIG. 1B
FIG. 1C

FIG. 2A

```
                                                     ------- Signature Region 2 --------

Eco    YLDEESREHFAGLCKLLESAGIAYTVNQR------LVRGLDYYNRTVFEWVTNSLGSQ-------GTVCAGGRYDGLVEQLGGRA    298
Yea    --NEKAKQGLDDI-ATLMKYTEAFDIDSFISFDLSLARGLDYYTGLIYEVVTSASAPPENASELKKKAKSAEDASEFVGVGSIAAGGRYDNLVNHFSEAS    368
Hum    --MKQALEGLGDL-KLLFEYLTLFGIDDKISFDLSLARGLDYYTGVIYEAVL-----------LQTPAQAGEEPL---GVGSVAAGGRYDGLVGMF-DPK    373

Ham    --NKQAVEGLGDL-KLLFEYLTLFGIDDKISFDLSLARGLDYYTGVIYAVL------------LQMPTGAGEEPW-----CGQCGCWRRYDGLVGMF-DPK    372
                                                                                  ↑ ↑↑↑↑↑↑

----- Motif 3 ------
Eco    T-------PAVGFAMGLERLVLLVQ----AVNPEFKADPVVDIYLVASGADTSQAAMALAERLR--DEL--PGVKL-MTNHGGGNFKKQFARADKWGARVA    383
Yea    GKKSTQIPCVGISFGVERIFSLIKQRINS-STTIKPTAT-QVFVNAFGGGKDWTGY-LPERMKVTKQLWDAGIEAEYVYKAKANPRKQFDTTKKAGCHIA    465
Hum    GRK----VPCVGLSIGVERIFSIVEQRLEALEEKVRTTET-QVLVAS----AQKLLE----ERLKLVSELWDAGIKAELLYKQNPKLLNQLQYCEEAGIPLV    463

Ham    GRK----VPCVGLSIGVERIFSIVEQRLEALEEKVRTTET-QVLVAS----AQKKLAG----GETKACLQLWDAGIKAELLYKKNPKLLNQLQYCEETGIPLV    462
                                                                    ↑↑                                  ↑

Eco    VVLGESEVANGTAVVKDL-----RSGEQTAVAQDSVAAHLRTLLG---------------------------    
Yea    VILGKEEYLEGKLRVKRLGQEFADDDGELVSAADIVPIVQEKLSQIHEDGLNEVTRLIKGL    526
Hum    AIIGEQELKDGVIKLRS-------------------VTSREEVDVRREDL--VEEIKRRTGQPLCIC-    509

Ham    AIIGEQELKDGVIKLRS-------------------VASREEVDVRREDL--VEEIRRRTNQPLYVC-    508
```

FIG. 2B

```
HIS  Eco  IGEVTDVVEKEMYTFEDRNGDSLTLRPEGTAGCVRAGIEHGL    97  (SEQ ID NO:25)
     Yea  YGEDS----KLIYNLEDQGGELCSLRYDLTVPFARYVAMNI    144  (SEQ ID NO:26)
     Hum  YGEDS----KLIYDLKDQGGELLSLRYDLTVPFARYLAMNKL    144  (SEQ ID NO:27)

THR  Eco  EKTGHWDNYKDAMFTTSSENREYCIKPMWCPGHVQIFMQGLKSYRDLP   352  (SEQ ID NO:28)
     Yea  ETSGHWANYKENMFTFEVEKETFGLKPMWCPGHCLMFKSRERSYRELP   448  (SEQ ID NO:29)
     Hum  MTSGHWQHYSENMFFFEVEKELFALKPMWCPGHSLMFDNRPRSWRELP   419  (SEQ ID NO:30)

SER  Eco  YGTGQLPKFAGDLFHTRPLEEADTSNYALIPTAEVPLTNLVRGEIID..EDDLP   257  (SEQ ID NO:31)
     Yea  SKTAQPSEFDEELYKVIDGEDEK.....YLIATSEQPISAYHSGEWFEKPQEQLP   273  (SEQ ID NO:32)
```

FIG. 3A

```
HIS   Eco   LVRGLDYYNRTVFEVV----n=7----GTVCAGGRYDGLVEQL   294   (SEQ ID NO:33)
      Yea   LARGLDYYTGLIYEVV----n=29---GSIAAGGRYDNLVNMF   364   (SEQ ID NO:34)
      Hum   LARGLDYYTGVIYEAV----n=15---GSVAAGGRYDGLVGMF   370   (SEQ ID NO:35)

THR   Eco   GEGAFYGPKIEFTLYDCLDRAWQCGTVQLDFSLPSRLSASYVG...EDNERKVPVMI   510   (SEQ ID NO:36)
      Yea   GDAFYGPKIDIMISDALRRWHQCATIQLDFQLPNRFELEFKSKDQDSESYERPVMI   598   (SEQ ID NO:37)
      Hum   GDGAFCGPKIDIQSKDAIGRYHQCATIQLDFQLPIRFNLTYVS..HDGEDKKRPVIV   577   (SEQ ID NO:38)

SER   Eco   TGDMGFGACKTYDLEWIPAQMTYREISSCSNVWDFQARRMQARC..RSKSDKKTRLVH   386   (SEQ ID NO:39)
      Yea   SGELNWAAAKKYDLEAWFPYQKEYKELVSCSNCTDYQSRNLEIRCGIKMGDREKKYVH   399   (SEQ ID NO:40)
```

ASSAY USING RECOMBINANT HISTIDYL-TRNA SYNTHETASE

BACKGROUND OF THE INVENTION

The aminoacyl-tRNA synthetases constitute a group of about twenty proteins which play a crucial role in translating the genetic code by catalyzing the reaction joining amino acids to their cognate tRNAs. Despite widespread common functionality, their structures are very diverse. Primary structures of almost all 20 bacterial and yeast synthetases have been ascertained. This research has led to the recognition of two major synthetase classes based upon both crystallographic and primary structure analysis. These findings have greatly advanced our understanding of the evolutionary pathways that led to the functional preservation of synthetases despite their remarkable structural diversity.

In contrast to the data from lower eukaryotes, far less structural information is available for synthetases from higher eukaryotes. The only nucleotide sequences of mammalian synthetases so far available are those of the glutaminyl-synthetase (Fett, R. et al. (1991) *J. Biol. Chem.* 266: 1448–1455), aspartyl-synthetase (Jacobo-Molina et al. (1989) *J. Biol. Chem.* 264: 16608–1612), threonyl-synthetase (Cruzen et al. (1991) *J. Biol. Chem.* 266: 9919–9923), valyl-synthetase (Hsieh et al. (1991) Biochem. J. 278: 809–816), tryptophanyl-synthetase (Garret et al. (1991) *Biochemistry* 30: 7809–7817) and histidyl-synthetase (Tsui et al. (1987) *Nucleic. Acids. Res.* 15: 3349–3367; Tsui et al. (1987) *Gene* 61: 349–361).

The histidyl-tRNA synthetase (HRS) has been particularly interesting since it is a frequent target of autoantibodies relating to human autoimmune diseases including myositis, polymyositis and dermatomyositis (Nishikai et al. (1980) Arthritis Rheum. 23: 881–888). Four other synthetases have also been found as targets of autoantibodies—threonyl-synthetase (Mathews et al. (1984) *J. Exp. Med.* 160: 42–434), alanyl-synthetase (Bunn et al. (1987) Mol. Biol. Med. 4: 21–36), glycyl-synthetase, and isoleucyl-synthetase (Targoff, I. N. (1990) *J. Immunol.* 144: 1737–1743). However, these synthetases were only rarely found to be an autoimmune target.

Patients having these autoantibodies form a distinct group clinically, and perhaps genetically (Love et al. (1991) *Medicine* (Baltimore) 70: 360–374). Recent studies on the mechanisms of anti-HRS induction and regulation suggest that the native human enzyme is the antigen which selects and sustains the immune response, preceding clinical illness (Miller et al. (1990) *J. Clin. Invest.* 85: 468–475; Miller et al. (1990) *Proc. Natl. Acad. Sci. U.S.A.* 87: 9933–9937).

Assays for detecting HRS in serum have been developed (Biswas et al. (1987), *Journal of Immunological Methods* 98: 243–248) and have proven very useful for detecting autoimmune diseases related to HRS in human serum. To produce these assays purified HRS protein was isolated from HeLa cells using high performance liquid chromatography (HPLC). The isolated HRS protein was then bound to an ELISA plate and incubated in the presence of human serum (Biswas et al. (1987), *Journal of Immunological Methods* 98: 243–248). Detectable binding of antibodies in the serum to the bound HRS protein indicated an autoimmune disease state.

HRS proteins have also been isolated from calves' liver (Targoff et al., *J. Immunol.,* 138:2874–2882 (1987). However HRS proteins isolated from calves' liver or HeLa cells were very unstable, even when stored at −80° C. For this reason, ELISA experiments using such isolated HRS proteins had to be performed rapidly following isolation. In addition, isolating HRS using HPLC is a time-consuming and difficult process.

The HRS gene from a SV40 transformed fibroblast cell line was cloned and expressed in COS 1 cells (Tsui et al. *Nucl. Acid. Res.* (1987) 8: 3349–3367). Three regions of extensive homology between the Human HRS and a hamster HRS clone were discovered. In addition, Ramsden et al. (*Journal of Immunology* (1989) 143: 2267–2272) has epitope mapped the expressed product of a cloned HRS gene. However, in these experiments the HRS cDNA was transiently transfected into COS 1 cells which already express an endogenous HRS. For this reason, background binding from expression of the endogenous enzyme made determining the amount of binding from the transfected clone difficult.

Although others have disclosed methods of isolating HRS from HELA cell extracts, these proteins were only weakly immunogenic in assays for autoimmune diseases. It would be very advantageous to provide a HRS which was much more sensitive to antibodies than the previously disclosed protein.

SUMMARY OF THE INVENTION

One preferred embodiment of the present invention is recombinant Histidyl tRNA synthetase produced by transfection into non-mammalian host cells, wherein the recombinant Histidyl tRNA synthetase is substantially free from endogenous Histidyl tRNA synthetase produced in the host cells.

Another aspect of the present invention is a method for determining the presence of an autoimmune disease in a mammal. The diseases are advantageously myositis, polymyositis, or dermatomyositis. This method includes isolating a sample of body fluid from a mammal wherein the body fluid contains antibodies. Following isolation of body fluid, preferably blood serum, the fluid can be advantageously stored for greater than 24 hours. The body fluid is then contacted with recombinant Histidyl tRNA synthetase produced in a non-mammalian host cell, preferably an insect cell. This contact is more preferably an ELISA, with the Histidyl tRNA most preferably being stored at a temperature within the range −80° C. to 25° C. the recombinant Histidyl tRNA synthetase being substantially free of endogenous Histidyl tRNA synthetase from the host cell. After contacting the recombinant Histidyl tRNA synthetase with the body fluid the presence or absence of binding of the antibodies to the recombinant Histidyl tRNA synthetase is detected, wherein detectable binding of the antibodies to the recombinant Histidyl tRNA synthetase indicates the presence of an autoimmune disease in the mammal.

Still another embodiment of the present invention is a method for determining the presence of an autoimmune disease in a mammal. The autoimmune disease is preferably polymyositis, myositis and dermatomyositis. In this method a sample of body fluid from a mammal is isolated, with the body fluid having antibodies. The next step of the method is obtaining a peptide of Histidyl tRNA synthetase with the peptide being produced in non-mammalian host cells wherein the Histidyl tRNA synthetase is substantially free of endogenous Histidyl tRNA synthetase from the host cell. Preferably the peptide is the first 60 amino acids of Histidyl tRNA synthetase. Alternatively, the peptide is the first 47 amino acids of Histidyl tRNA synthetase. The peptide most preferably comprises an amino acid sequence that contains less than the full-length amino acid sequence of Histidyl tRNA synthetase with the peptide containing at least one antigenic determinant present in full-length Histidyl tRNA synthetase. The next method step is contacting the isolated body fluid, preferably blood serum, with the peptide and detecting the presence or absence of binding of the antibodies to the peptide of Histidyl tRNA synthetase. Most advantageously, the contacting step is an ELISA and detectable binding of the antibodies in the body fluid to the peptide fragment indicates the presence of an autoimmune disease in the mammal.

Yet another embodiment of the present invention is a kit for determining the presence of antibodies from an autoimmune disease in the blood serum of a mammal. This kit comprises recombinant Histidyl tRNA synthetase produced by expression in a non-mammalian host cell, a vessel for performing an assay to detect binding of the antibodies to the recombinant Histidyl tRNA synthetase, and reagents for detecting the binding of the antibodies to the recombinant Histidyl tRNA synthetase, wherein positive binding indicates the presence of an autoimmune disease in the mammal. In this kit the vessel is preferably a microtiter plate, and the mammal is a human. Advantageously, the reagents for detecting the binding of the antibodies to the recombinant Histidyl tRNA synthetase comprise labeled anti-human antibodies. In addition, the detection reagents preferably comprise reagents for performing an ELISA.

DESCRIPTION OF THE FIGURES

FIGS. 1A–1C. Hybridization of amplified HRS DNA with oligonucleotides specific for Hep G2 HRS or for the published sequence. FIG. 1A is a schematic diagram of PCR amplified fragments and positions of primer sites for PCR. 5' and 3' fragments of the HRS cDNA encompassing the entire coding region were amplified with Taq DNA polymerase from Hep G2 HRS cDNA (positive control), IMR 90 and HFM-1 cell lines. Fragments corresponding to exon 6 through exon 8 and exons 8 and 10 separately were amplified from genomic DNA. FIG. 1B shows a direct sequence analysis of PCR-amplified Hep G2 HRS cDNA corresponding to mid-exon 8 and mid-exon 10. Boxes represent regions of non-identity between Hep G2 and the published sequence. Oligonucleotides specific for Hep G2 (983 and 987) or for the published sequence (2491 and 986) were used to probe PCR amplification products. Oligonucleotides 2491 and 986 were also used for low stringency PCR amplification from genomic DNA to generate positive controls for the published sequence (lanes 2 and 4). The amplified DNA hybridized to Hep G2 specific probes. In contrast, oligonucleotides specific for the published sequence hybridized only the DNA amplified in order to generate a positive control.

FIGS. 2A–2B. Alignment of the predicted amino acid sequences of E. coli, yeast, and human HRS. Motifs 1, 2 and 3 (Eriani et al. (1990) Nature 347: 203–26) and signature regions 1 and 2 (see Discussion) are indicated above the E. coli sequence. The 32 amino acid shared motif is underlined. E. coli, yeast, and human are identical; * there is a conserved substitution. Arrows beneath the predicted hamster sequence indicate amino acids likely to be incorrect based upon conservation among the others. The alignment was modified by hand from an alignment produced by the Clustal program in PCGene.

FIG. 3A–3B. Signature regions. Computer generated alignments were modified by hand to maximize alignment within an amino acid family.

DETAILED DESCRIPTION

We have discovered that the recombinant histidyl tRNA synthetase (HRS) protein produced in non-mammalian host cells provides unexpectedly superior results when used as an antigen in assays for determining autoimmune diseases in human serum. We have advantageously produced such recombinant HRS protein in non-mammalian hosts, such as insect cell lines, by inserting the human histidyl tRNA synthetase (HRS) gens into a baculovirus expression system. We have also found that antigenic peptide fragments of this protein have far greater affinity for autoimmune antibodies in human serum than would have been expected from studies on HRS purified from HeLa cells.

Although, as discussed in the background, others have expressed recombinant HRS in COS 1 cells, these cells contain an endogenous HRS protein which interferes with studies relating to the transfected HRS gene. We have found that the HRS produced by insect cells has no antigenic cross-reactivity with the human HRS and therefore provides a very advantageous host for producing large quantities of isolated HRS. As discussed herein the term isolated, when referring to a protein or peptide, includes those molecules that have been purified to greater than their naturally occurring concentration.

To express the HRS antigen for immunologic experiments, and to study the control of its synthesis, we isolated a cDNA encoding human HRS from the human hepatoma cell line, HepG2. This sequence is available as Accession No. Z11518 in the European Molecular Biology Labs (EMBL) database. The cDNA sequence, determined by direct sequencing of PCR-amplified fragments, was markedly different from the published sequence of the human enzyme (Tsui et al. (1987) Nucleic. Acids. Res. 15: 3349–3367). Differences within the coding region included multiple nucleotide substitutions, insertions and deletions resulting in frameshifts which led to a substantial difference in the protein's predicted primary structure.

Although it was possible that an allelic variation of the HRS gene had been isolated, numerous experiments with specific PCR amplification determined that the human genome only carried one copy of the HRS gene. In addition, analysis of nucleotide sequences from fetal myoblast and fibroblast cell lines confirmed the accuracy of our sequence. We concluded that sequencing errors led to publication of the incorrect HRS nucleotide sequence by Tsui et al., Nucl. Acid Res. (1987) 8: 3349–3367.

As a first step in sequencing and expressing a recombinant clone, we isolated a cDNA sequence corresponding to the HRS protein in HepG2 cells. The newly determined sequence differed in 48 places, including insertions and deletions, from the previously published sequence by Tsui et al. By sequence specific probes and direct sequencing, we established that only the newly determined sequence was present in genomic DNA. Further, we have sequenced 500 bases upstream of the translation start site to search for regulatory regions.

The predicted amino acid sequence derived from the cDNA clearly exhibited all three of the expected motifs recognized in Class 2 aminoacyl-tRNA synthetases. Alignment of E. coli, yeast, and mammalian predicted amino acid sequences for three of the four members of the class 2a subgroup (his, pro, ser, and thr) exhibited strong preservation of amino acid specific signature regions proximal to motifs 2 and 3. These potentially represented the binding regions for the proximal acceptor step and the amino acid during translation.

The amino acid sequence of the first two exons of human HRS predicted a structure having a 32 amino acid helical motif. This type of motif was first described in human QRS, a class 1 synthetase, and is also found in a yeast RNA polymerase, a rabbit termination factor, and both bovine and human WRS. As these proteins are all RNA binding factors it suggests that the first two exons of human HRS may contain an RNA binding motif.

DNA Sequence Analysis

As discussed previously, the cDNA sequence we determined by direct sequencing of PCR-amplified fragments (without cloning) differed markedly from the published HRS sequence obtained from an SV40-transformed human fibroblast line (Tsui et al. (1987) *Nucleic. Acids. Res.* 15: 3349–3367). The HepG2 HRS coding region has 39 nucleotide substitutions, 6 insertions, and 3 deletions resulting in several frameshifts compared to the published sequence.

Several possibilities besides sequencing errors could explain the discrepancy, including the existence of two genes or of alternatively spliced forms of a single transcript from two tissue sources. To choose among these possibilities, we synthesized HRS cDNA from the IMR 90 and HFM-1 fetalmyoblast cell lines. Total RNA was isolated followed by PCR amplification of two overlapping DNA fragments encompassing the entire HRS coding region. To rule out the possibility of PCR carryover, we amplified a genomic region spanning exon 6 through exon 8 which includes 2 small introns, according to the intron-exon boundaries published for the hamster HRS gene (Tsui et al. (1987) *Gene* 61: 349–361). Finally, exon 8 and exon 10 were separately amplified from human genomic DNA in an attempt to locate the published sequence somewhere in the genome (FIG. 1A). All the PCR primers (except as noted below) were chosen to match regions of exact agreement between the sequences but to flank regions of discrepancy.

For each amplification, a single product of the expected size was obtained. The products were probed with oligonucleotides specific for HepG2 HRS or for the published sequence. (FIGS. 1B and 1C). HepG2 5' frag and 3' frag served as positive controls for slot blot hybridization analysis. Two primers (2491 and 986—Table 1) corresponding to the published sequence mid-exon 8 and mid-exon 10 were used for PCR amplification at low stringency (45° C. annealing) to generate a positive control for the published sequence.

Only HepG2 HRS-specific oligonucleotides hybridized under stringent conditions with the corresponding DNA sequences. In contrast, only control PCR products, produced at low stringency with primers containing published sequences, would hybridize with the probes specific for the published sequence. Hybridization of duplicate gel blots with oligonucleotide probes (Table 1), corresponding to the Hep G2 (probe 18) or the published sequence (probe 19) for the end of exon 7 also exhibited signal only for Hep G2 (data not shown). These results clearly indicated that only the Hep G2 HRS sequence is present in the human genome. At the conclusion of these experiments, the entire coding sequence of HRS cDNA from cell line HFM-1 was determined by direct sequencing and was found to be identical to the Hep G2 sequence.

TABLE 1

Oligonucleotide Primers for PCR Amplification

| PRIMER NUMBER | SEQ ID NUMBER | | COMMENTS |
|---|---|---|---|
| | | UPSTREAM SEQUENCE | |
| 3 | 1 | GGCTGGGGCAACCACCGCAG | 5' UT |
| 984 | 2 | TCTCCTTTGACCTGAGCCTTG | beg. exon 10 |
| 12 | 3 | AGAATGAGATGGTGGGAGAGAAGGG | beg. exon 8 |
| 10 | 4 | GCCTGAAGATCATGTGCGAGATCC | mid exon 6 |
| 983 | 5 | TTGCACCtGAgGTGGCTGAcCGC | mid exon 8, probe Hep G2 |
| 2491 | 6 | TTGCACCaGAaGTGGCTGAtCGC | mid exon 8, probe publ. |
| 2 | 7 | GCAGAGCGTGCGGCGCTGGA | beg. exon 1 |
| 1102 | 8 | TGCGTGGGGAGACATCCGGGG | intron 1 |
| 2736 | 9 | GAGGCTCTCTAGGCGTGCG | 90 bp 5' to the ATG |
| | | DOWNSTREAM SEQUENCE | |
| 4 | 10 | CAGACTGGACTAAGCCTCCTGGGCC | 3' UT |
| 16 | 11 | TGGGTTCTTCTTGTACAGCAGG | exon 11 |
| 985 | 12 | AGTCTCTGTTCCACGATGGAGAA | end exon 10 |
| 17 | 13 | CCACCATGGTTGCTGGACATAGTC | end exon 8 |
| 987 | 14 | ACACTGCCCACAcCCAgGGGCTC | mid exon 10, probe HEP G2 |
| 986 | 15 | ACACTGCCCACA-CCA-GGGCTC | mid exon 10, probe publ. |
| 18 | 16 | TgTCcAGcTTGTCtACTGAG | end exon 7, probe HEP G2 |
| 19 | 17 | TaTCcAGcTTGTCtACTGAG | end exon 7, probe publ. |
| 421 | 18 | CTTGGGGGTTTTGAGCACAAATT | end exon 2 |
| 2597 | 19 | CCACTTGAGCCGCCTGCTGTCT | 9 bp 5' to the ATG |
| 2755 | 20 | GGCTACTAAGGGAACTTGGG | 158' bp 5' to the ATG |

Analysis of the sequence differences between the Hep G2 gene and the published sequence revealed that the changes we discovered in the HRS sequence were not random. At the nucleotide level Hep G2 HRS shared substantially more similarity with yeast HRS (Natsoulis et al. (1986) *Cell* 46: 235–243) than the Tsui et al. sequence (47.5% versus 40.9%). The sequence between the first in-frame methionine (ATG) codon and the stop codon in the cDNA encodes a 1527 bp open reading frame of 509 amino acids. The protein encoded by this open reading frame would have an approximate molecular weight of 57,410 daltons.

Figure 2A:
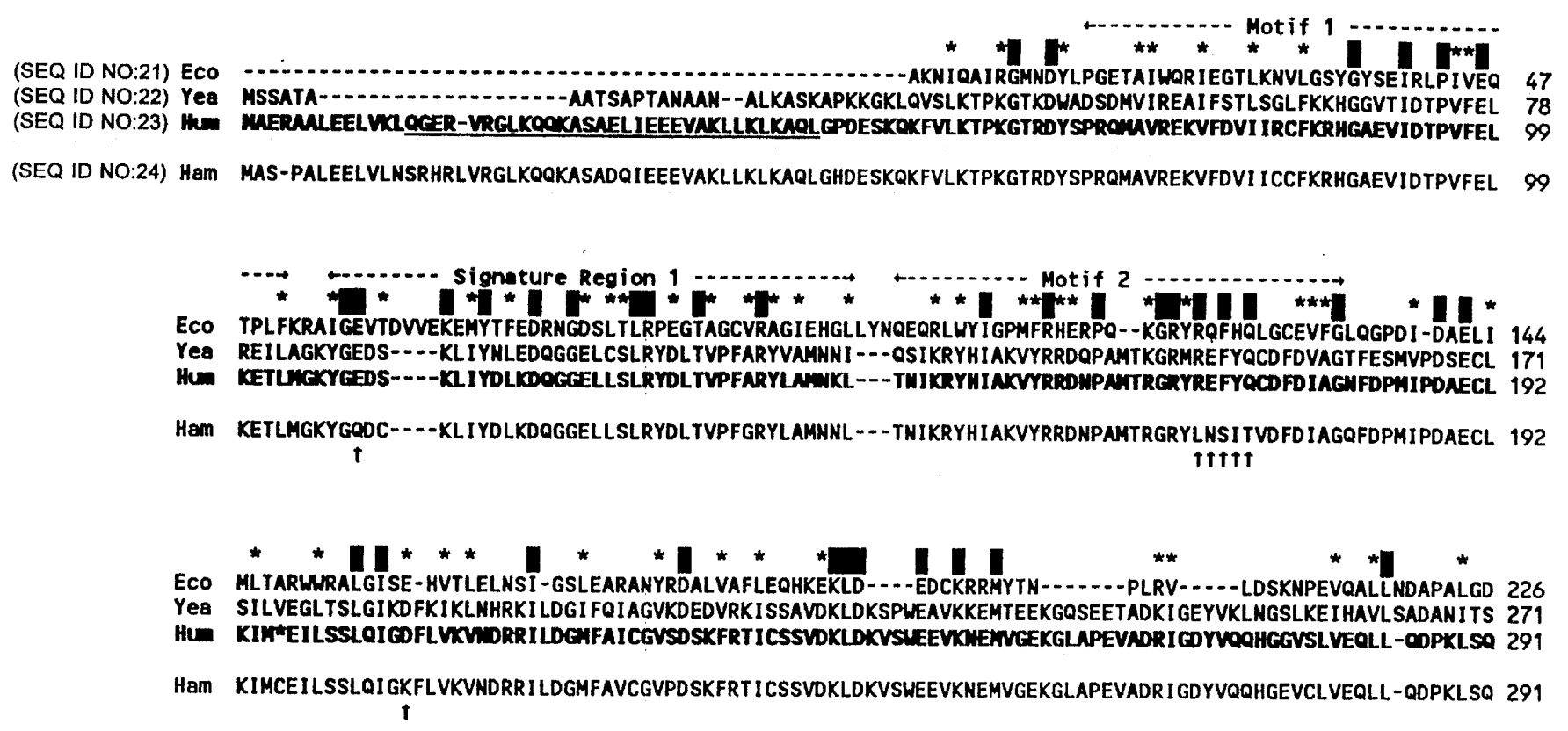

The predicted amino acid sequence of the human HRS shares considerably more homology with yeast HRS than the previously published sequence, particularly in the three structural motifs recently identified in Class 2 synthetases (FIG. 2). Among 37 amino acids in motif 1, eighteen are identical and six are conservative substitutions between yeast and human. In this same region, four amino acids are identical and eight conservatively substituted among *E. coli* (Freedman et al. (1985) *J. Biol. Chem.* 260: 10063–10068), yeast, and human. Among thirty-six amino acids in motif 2, thirty are identical and four are conservative substitutions between yeast and human. In addition, nine amino acids are identical and eleven conservatively substituted among *E. coli*, yeast, and human. In motif 3, among twenty-eight amino acids, fifteen are identical and six conservatively substituted between yeast and human. Also in motif 3, seven amino acids are identical and seven conservatively substituted among *E. coli*, yeast, and human. The three species share 78 identical and 89 conservatively substituted amino acids for an overall homology of 31.7 percent. In the motif regions, the hydrophobicity plots of the three proteins, determined by the technique of Kyte and Doolittle with the SOAP program in PC/GENE using a window of 11 amino acids, are nearly superimposable (data not shown).

5' Untranslated Region

To obtain a previously unknown sequence 5' to the translation start site, we performed inverted PCR. We first amplified and directly sequenced intron 1 of the HRS gene to find a convenient restriction site. Primer pairs 2 and 421 (Table 1) corresponding to the beginning of exon 1 and the end of exon 2 were used for this amplification. A two step protocol was employed to obtain a previously unknown 530 bp sequence upstream from the translation start site, taking advantage of the sequence information on intron 1. Ava I digestion of genomic DNA followed by amplification with primers 2597 and 1102 (Table 1) yielded an approximately 200 bp fragment outside the boundaries of known sequence. Based on the sequence of this fragment, we designed primers 2755 and 2736 to amplify, by inverse PCR, an additional 330 bp of upstream sequence using the Taq I restriction enzyme. To confirm the identity of the upstream sequence obtained by inverse PCR, we carried out genomic amplification of the region, including part of exon 1 in addition to the 5' untranslated region. This PCR product was directly sequenced with Taq DNA polymerase using the DNA Sequencing System (Promega) and was found to be identical with the sequence obtained by inverse PCR.

Mapping of Transcription Initiation

To determine the 5' end of the HRS mRNA isolated from the Hep G2 and HeLa cell lines, we used primer extension analysis with two different $^{32}$p labeled oligonucleotide primers complementary to the sequence from nucleotide +4 to +27 and from −137 to −158. In each case, one major extended product was observed in two cell lines, suggesting that the transcription initiates 378 to 382 nucleotides behind the ATG start codon. Two different P-labelled oligonucleotide primers hybridizing 240 and 400 nucleotides from the transcription start site were used for primer extension analysis. The primers were annealed to total RNA from Hep G2 and HeLa cells and extended by reverse transcriptase. The length of reverse transcripts was determined on a sequencing gel. A sequence ladder was obtained by using the primer extension ologonucleotide −137 to −158 as a sequencing primer and PCR-amplified genomic fragment as a template. The position of the start site was determined from a sequencing reaction initiating from the same primer using amplified genomic DNA as a template. Several smaller extended products, observed only with the primer hybridizing downstream from the 5' end of the coding sequence, most likely represent false start sites due to secondary structure in the mRNA. The sequence upstream from the start site did not contain the TATA or CCAAT motifs. Instead, potential binding sites for the transcription factor SP1 were found in the 5'-flanking region.

Genomic PCR Amplifications

PCR grade human DNA was prepared from whole blood as previously described (Higuchi, R. (1989) in *PCR Technology. Principles and Applications for DNA Amplification*, Erlich, H.A. Ed. pp. 31–38, Stockton, N.Y.). Primers 10 and 17 (Table 1 and FIG. 1*a*) were used to amplify a genomic region covering exons 6–8 that included the two small introns. Amplification was performed with 2.5 U of Taq polymerase (1 min at 94° C., 1 min at 65° C., and 2 min at 72° C. for 30 cycles).

Two sets of primers were used to separately amplify exons 8 and 10 from genomic DNA. Amplification was carried out with primer pairs 12 and 17 (Table 1) for exon 8 (1 min at 94° C., 1 min at 60° C., and 1 min at 72° C.; 30 cycles) and primer pairs 984 and 985 for exon 10 (1 min at 94° C., 1 min at 65° C. and 2 min at 72° C.; 30 cycles) Products of genomic PCR amplifications were used for hybridization as discussed below.

Slot-Blot Hybridization

PCR products (200 ng DNA) were heat-denatured (5 min, 100° C.), diluted to 200 µl with 6X SSC (0.9 M NaCl, 90 mM sodium citrate, pH 7.0), and 100 µl aliquots were applied to a Nytran filter (Schleicher and Shuell, Inc.) pre-soaked in 6X SSC using a slot-blot apparatus. The filter was baked for 1 hour at 80° C. Single strips were hybridized to $^{32}$P-labelled oligonucleotides specific to either the Hep G2 HRS or to the published HRS sequence by Tsui et al. Hybridization continued overnight at 42° C. in 5X SSPE (0.75 M NaCl, 50 mM NaH$_2$PO$_4$, 5 mM EDTA), 5X Denhardt's solution, and 0.5% SDS, followed by washing several times at room temperature in 2X SSPE, 0.5% SDS and a 30 minute wash at 55° C. in 2X SSPE, 0.5% SDS.

Inverse PCR

To amplify a previously unknown regions upstream from the translation start site of the HRS gene, we employed the inverse PCR procedure (Triglia et al. (1988) *Nucleic. Acids. Res.* 16: 8186). Two sets of enzymes were used for chromosome walking. Genomic DNA (3 µg) was first cleaved with Ava I and ligated with T4 DNA ligase in a dilute DNA solution (<3 µg/ml). The resulting circular molecules were cut at an internal site with Bgl I and amplified with primers 2597 and 1102 (Table 1) (1 min at 94° C., 1 min at 60° C. and 2 min at 72° C., 30 cycles). Genomic DNA was then cut with Taq I, ligated, re-cut with HglA1 and amplified with primers 2755 and 2736 (Table 1) under the conditions described above. PCR products were directly sequenced by well known methods.

Primer Extension

Synthetic oligonucleotides complementary to the HRS mRNA were end-labelled with T4 polynucleotide kinase, hybridized to total RNA from Hep G2 or HeLa cell lines and extended with reverse transcriptase. A 20 µl mixture containing 50 µg RNA, 1.5×10$^5$ cpm of $^{32}$P-labelled primer, 80% formamide, 0.4M NaCl, 40 mM PIPES (pH 6.4), and 1 mM EDTA was denatured at 80° C. for 5 min and hybridized at 33° C. overnight. The hybridized RNA/DNA was precipitated with ethanol, resuspended in 20 µl of reverse transcription buffer (50 mMTris HCl (pH 8.3), 50 mM KCl, 6 mM MgCl$_2$. 1 mM DTT, 1 mM each dNTP, 1 U/µl RNAsin, 25 µg/µm 1 actinomycin D, and 20 U AMV reverse transcriptase (Life Sciences, Inc.) and incubated at 41° C. for 1 hour. The reaction was stopped with 1 µl 0.5M EDTA and the RNA was hydrolyzed with 2 µl 2N NaOH at 37° C. for 30 minutes. The extension products were extracted, ethanol-precipitated, separated on a 6% polyacrylamide/8M urea gel, and detected by autoradiography.

The sequence of human HRS we have determined allows HRS to fit comfortably with the Class 2 synthetases, unlike the previously published Tsui et al. sequence.

Multiple errors in the previously published human HRS cDNA sequence, including both nucleotide substitutions and frameshifts, led to an 8.9% difference at the amino acid level. Alignment of the sequences of *E. coli*, yeast, and human (Hep G2) alongside the predicted sequence for the published hamster sequence (Tsui (1987) *Gene.* 61: 349–361) is shown in FIGS. 2A and 2B. The hamster sequence diverges from human in areas conserved between yeast and human and even in areas conserved among the *E. coli*, yeast and human, suggesting that it, too, contains errors. Areas likely to contain sequencing errors are indicated by arrows beneath the hamster sequence in FIG. 2.

The determination of the human HRS sequence, along with the recently completed human TRS sequence (Cruzen et al. (1991) *J. Biol. Chem.* 266: 9919–9923), now allows sequences of Class 2a synthetases for the same amino acid from a prokaryote (*E. coli*), a lower eukaryote (yeast), and a higher eukaryote (human) to be compared. From the published analyses of Class 2 synthetases—first, by Eriani, et al. (*Nature* (1990) 347: 203–26), and more recently by Cusak, et al. (*Nucleic. Acids. Res.* (1991) 19: 3489–3498)—it has been possible to recognize those structural elements that have been preserved during the presumed horizontal evolution of a primitive parent synthetase to the ten enzymes which comprise the family. The crystal structures of two of these synthetases, including one with the cognate tRNA bound, has allowed certain recognition of the ATP binding site and of the region which binds the 3' CCA end common to every tRNA. Motif 2 and Motif 3 are concerned with binding the stem and the ATP, respectively. Because the overall chemical reaction catalyzed by these enzymes involves the esterification of the carboxyl group of an amino acid first to ATP, and then to a hydroxyl on the ribose of the terminal adenosine, these are just the features which must be conserved during both the horizontal evolution—from a parent protein to progeny for ten different amino acids—and the vertical evolution—from species to species.

There are, however, additional requirements for vertical evolution. The amino acid cavities for the tRNA recognition motifs need to be evolutionarily preserved, along with the anti-codon and the most distal base pair(s) of the acceptor stem (Hiraki et al. (1987) *Kaku. Igaku.* 24: 1483–1489) have pointed out the region between Motifs 1 and 2 that encompass loop L1, beta sheet B2 and helix H9 contain some amino acid specific sequences as does the region encompassing two strands of the active site beta sheet, βA3, and βA4. The three HRS sequences, the three TRS sequences and the *E. coli* and yeast SRS sequences—three of the four members of Class 2a—allow a clearer view of these two regions, which lie outside the motifs, in which strong vertical preservation suggests that they are regions conserved for these purposes.

In FIG. 3a, the region just proximal to motif 2, designated signature region 1, is aligned for these sequences. The strong vertical preservations within all three families is evident. For HRS, among 42 amino acids, 10 are identical, 12 are conservatively replaced, and three runs of three amino acids are conserved. For TRS, among 48 amino acids, 20 are identical, 5 are conservatively replaced and there are runs of nine, seven, and four conserved amino acids. For SRS, among 55 amino acids, 15 are identical, 11 are conservatively replaced, and there is one run of five and four runs of three conserved amino acids, although introduction of two gaps is necessary. What is striking, however, is that whereas in motif 2 it is easy to align all of the eight sequences, in signature region 1, the three groups are wholly different.

The alignment of a second area, designated signature region 2, is shown in FIG. 3B. This region is comprised of the β strands A3 and A4 in *E. coli* SRS. Here the amino acid conservation is even stronger. Allowing for a single variable gap in the middle of each HRS, among 32 amino acids, 18 are identical and seven are conservatively replaced. In addition, there are conserved runs of eight, six, five and three amino acids. In TRS, with allowance for a gap in *E. coli* and human, among 57 amino acids, 22 are identical and 11 are conservatively replaced. Also, there are conserved runs of four, five, six and six amino acids. In SRS, among 59 amino acids, 24 are identical and 13 are conservatively replaced, including a conserved run of ten, four runs of four, and two runs of three conserved amino acids. Again, the three groups differ strikingly from one another, but in each group preservation almost always exceeds preservation within the motifs.

Based on the crystal structures of the closely related class 2a synthetase, *E. coli* SRS and of the less closely related class 2b yeast DRS (Ruff et al. (1991) *Science* 252: 1682–1689) these signature regions are likely to interact with the proximal acceptor stem and the amino acid, respectively. The low overall homology between some *E. coli* and yeast pairs and the abnormal charging of a yeast tRNA within *E. coli* have suggested the possibility that a synthetase might have changed its commitment to a particular amino acid during evolution. The existence of the vertically preserved signature regions shown in FIG. 4 is the strongest evidence so far of the continuous evolutionary relatedness of family members.

The amino terminal 60 amino acids in human HRS, which precede Motif 1 and are in a region known to vary greatly among synthetases even within the same family, has been discovered by Fett and Knippers to have a significant homology to a 57 amino acid motif which is repeated three times in the middle of the anomalously large human QRS (Fett, R. and Knippers, R. (1991) *J. Biol. Chem.* 266: 1448–1455). The location of this shared motif, which is wholly contained within the first two exons of HRS, raises the possibility that the two most proximal exons and the first intron of HRS shuffled to QRS. What adds particular interest to this possibility is the fact that QRS is a Class 1 enzyme whose gene is located on human chromosome 1 and HRS is a Class 2 enzyme whose gene is located on human chromosome 5. A recent search of Genbank and EMBL by the TFasta program of the Wisconsin GCG Sequence Analysis Software Package, carried out by the Advanced Scientific Computing Facility of the Frederick Cancer Research Center, however, shows that the center of this 60-amino acid stretch (aa residues 14 to 45—FIG. 2) has substantial homology to a variety of other known genes.

Besides human QRS and hamster (but not yeast) HRS, yeast RNA polymerase C-40 gene (Accession number M15499), rabbit eukaryotic release factor (Accession number m33460), and both bovine (Accession numbers X52113, M74074, J05334, X53918) and human (Accession number M61715) tryptophanyl tRNA synthetases are closely related. These are all proteins which bind or interact with RNA, suggesting the possibility, reinforced by the predicted helical structure, that this is a nucleic acid binding motif.

Following the determination and analysis of the cloned DNA fragment, we expressed the Hep G2 gene in a baculovirus expression system, and performed assays for human autoimmune diseases.

We and others had developed detection methods for HRS using purified Hela cell HRS in an ELISA, but the procedures were expensive and difficult to perform. Since we were interested in studying the origins of autoimmunity, in particular focussing on autoimmune muscle diseases (myositis), we decided to research antibody binding to recombinant HRS.

Expression of HRS in Baculovirus Expression System

Total RNA was isolated from Hep G2 cells using the RNAzol method (Chomczynski, P. and Sacchi, N. (1987) Anal. Biochem. 162, 156–159). cDNA was synthesized from 2.5 µg of total RNA in a 20 µl reaction containing 10 mM Tris-HCl (pH 8.3), 50 mM KCl, 1.5 mM $MgCl_2$ (1X PCR buffer, Perkin-Elmer-Cetus), 0.25 mM dNTP, an oligo(dT) primer, and 10 U of AMV reverse transcriptase (Boehringer, Mannheim). After incubating at 42° C. for one hour, reactions were heated at 65° C. for 10 min, and 2 µl was used for PCR.

PCR reactions were carried out in a final vol of 100 µl and contained 1X PCR buffer, 200 µM dNTP, 250 ng each of oligonucleotide primers flanking the coding region (Table 1—primers 3 and 4) and 2.5 U of Taq polymerase (Perkin-Elmer-Cetus) (1 min at 94° C., 1 min at 55° C., 3 min at 72° C. for 40 cycles). The oligonucleotides were constructed from the published HRS-human sequence obtained from an SV 40 transformed human fibroblast line (Tsui, F. W. and Siminovitch, L. (1987) *Nucleic. Acids. Res.* 15: 3349–3367). The resulting 1.6 kB DNA fragment was directly sequenced using the protocol we described previously (Raben et al. (1991) *Diabetes* 40: 118–122). Overlapping sequences were obtained for both strands of the cDNA.

RNA from human fibroblast line, IMR 90, and human fetal myoblast line, HFM-1, (the kind gift of Dr. Lori Love) was reverse-transcribed using an oligo(dT) or primer 4 (Table 1) and subsequently amplified for 40 cycles with primer pairs 3 and 16 or 4 and 984 (Table 1 and FIG. 1A) to obtain two overlapping DNA fragments ("5' frag" and "3' frag") encompassing the entire coding region of HRS. Each PCR cycle consisted of 1 min at 94° C., 1 min at 68° C., and 2 min at 72° C. DNA fragments from IMR 90 and HFM-1 cell lines were used for hybridization analysis. 5' frag and 3' frag from the Hep G2 cell line served as controls for these experiments.

From PCR-amplified DNA, a 1.6 kb Spe 1 fragment containing the full HRS coding region was obtained and ligated into plasmid pBlueBac® (Invitrogen), linearized with NheI and dephosphorylated with calf intestinal alkaline phosphatase (CIAP). This plasmid vector has a strong polyhedron promoter to direct the synthesis of foreign gene products. Clones of pBlueBac-HRS having the HRS cDNA in the correct orientation were identified by standard methods, followed by plasmid purification. The resulting construct encoded a non-fusion protein with initiation at the HRS internal ATG, after homologous recombination with AcPNV, the insect baculovirus.[12]

To obtain recombinant virus, Sf9 cell monolayers were co-transfected with the recombinant vector (pBlueBac-HRS) and wild type baculovirus, purchased as linearized viral DNA from Invitrogen, by the calcium phosphate precipitation technique. $5 \times 10^6$ Cells were seeded in 25 $cm^2$ flasks in 4 ml of TNM-FH medium with 10% fetal calf serum (Gibco BRL/Life Technologies) and allowed to attach for 1 hour. 2 µg of linear AcNPV was mixed with 4 µg of pBlueBac-HRS in 0.75 ml of transfection buffer (25 mM hepes, pH 7.1, 140 mM NaCl, 125 mM $CaCl_2$). The DNA solution was added dropwise to the cells containing 0.75 ml fresh medium. After 4 hours, the medium was replaced with 5 ml of fresh complete medium and the cells were incubated at 27° C. The virus-containing inoculum was collected after 7 days and recombinant baculovirus was purified by plaque assay according to the method of Webb and Summers, with diluted transfection supernatants and 1% agarose overlay containing X-gal at 150 µg/ml. The recombinant plaques were easily distinguishable by blue coloration and then selected by their occlusion-negative phenotype. Putative recombinant viral isolates were purified through two rounds of plaque purification to obtain pure recombinant virus stocks. To confirm that isolates contained HRS DNA, genomic viral DNA was prepared according to Webb et al. (Webb, AC, et al., *BioTechniques* (1991) 11: 512–519) and amplified by PCR with insect specific oligonucleotide primers (Invitrogen) spanning the entire coding region of HRS. DNA was prepared from pelleted viral particles and then amplified with appropriate oligonucleotides by PCR. All tested isolates were positive for the presence of the insert sequence corresponding to the HRS cDNA.

The level of recombinant protein expression in baculovirus was assayed by Coomassie blue staining and autoradiography of metabolically labelled cell lysates after SDS-PAGE. For metabolic radiolabelling of recombinant protein, cells were seeded in a 24 well plate at a density of $0.5 \times 10^6$ cells/well, infected at a 5–10 multiplicity of infection (MOI) and incubated at 27° C. for various times. The cells were then incubated for 1 hour in methionine-free medium, and for the next 4 hours in medium containing 5 µg, $^{35}$S-methionine.

For production of recombinant protein, cells were infected at 1–10 MOI in 20 ml and incubated for 1 hour. Infected cells were seeded in 100 ml spinner flasks at a density of $2 \times 10^6$ cells/ml. Cultures were grown at room temperature and 55 rpm and then harvested between 44 and 48 hours post infection. Cells were washed twice with ice-cold PBS (7,3 mM $NaH_2PO_4$, 55 mM KCl, 74 mM NaCl, 6.8 mM $CaCl_2$, pH 6.2) and homogenized and a Dounce homogenizer in 20 ml of 10 mM Tris-HCl, pH 7.5, 5 mM $MgCl_2$ containing 0.1 mM PMSF, 0.25 µg/ml Leupeptin, 0.5 µg/ml Aprotinin, and 1 mM EDTA. Almost no HRS was found in the culture supernatant; all rHRS was found in cytoplasmic extracts of the infected cells.

Production of HRS in Other Non-mammalian Host Cells

Other methods of producing recombinant HRS in non-mammalian host cells are also anticipated. For example, cDNA encoding HRS can be ligated into a yeast expression plasmid, such as pYES2 (Invitrogen, San Diego, Calif.). Following ligation by standard methods known to those of skill in the art, the pYES2 plasmid is transfected into yeast strain INVSc1 (MATα his3-Δ1 leu2 trp1-289ura3-52) from Invitrogen (San Diego, Calif). Following incubation, the expressed protein is then isolated by standard methods from the INVSc1 cells. Other vectors and their corresponding non-mammalian host cells are also expected to advantageously produce rHRS.

Analysis of Expressed Protein

Proof that the infected cell cultures produced authentic HRS was obtained in the following ways:

(1) immunoprecipitation of both labelled and unlabelled cell supernatants with monospecific antibodies from sera of polymyositis patients demonstrated a single band which migrated in the identical position as HRS immunoprecipitated from normal human tissue cultured cell lines; (2) an enormous rise in activity of HRS in cell lines infected with recombinant virus but not in cell lines incubated with wild-type baculovirus, nor in uninfected cell lines similarly incubated and extracted; (3) removal of this new enzymatic activity by adsorption with agarose beads bound to monospecific antibodies to HRS but not bound to normal immunoglobulin. Enzymatic activity was measured by the method of Biswas et al. (*Journal of Immunological Methods*, 98 (1987) 235–241).

ELISA Assays Using Recombinant HRS

A specific ELISA assay for the presence of anti-HRS antibodies was developed using rHRS produced by the previously discussed baculovirus expression system. rHRS was not further purified and therefore, a control antigen used for all experiments consisted of similarly prepared protein preparations from wild type baculovirus infected cells. Optimal conditions for this assay were determined empirically using sera known to be positive and negative for antibodies against HRS (anti-Jo-1) by immunoprecipitation.

A crude form of HRS was obtained from baculovirus infected cells and the concentration of HRS was determined to be 200 µg/ml. Antigen and control protein extracts were diluted in buffer and incubated at room temperature for at least 2 hours, or at 4° C. overnight, on Immulon 1® flat bottom plates. The plates were then blocked with a blocking agent 10 mg/ml Bovine Serum Albumin and incubated at room temperature for at least 2 hours or at 4° C. overnight. The plates were then washed three times in PBS+Tween-20 0.1% and twice in distilled $H_2O$.

Serum diluted in buffer with blocking agent was added, and incubated, at room temperature for 2 hours. The plates were washed again and goat anti-human IgG conjugated to alkaline phosphatase diluted 1:2000 in buffer with the blocking agent was added. The plates were incubated at room temperature for another 2 hours, washed, and substrate was added at room temperature. Optical density measurements were then obtained.

Optimal binding of rHRS with the minimal amount of nonspecific baculoviral protein background binding was obtained using a buffer of PBS at pH 7.2 and blocking with Bovine Serum Albumin (BSA) at 10 mg/ml. Using plates prepared in this way, a positive signal was obtained from some anti-Jo-1 positive sera diluted 1:64,000. This dilution is far greater than would be detectable with HRS purified from HeLa cells. In previous experiments, serum dilutions of greater than 1:12800 were unable to detect binding to Hela cell purified HRS (Targoff et al. (1987) *J. Immun.* 138: 2874–2882). For this reason, the present invention provides an improved assay for determining patients with HRS-related autoimmune diseases.

To test the binding specificity of anti-Jo-1 to rHRS we compared sera from myositis positive and negative patients. Nine known anti-Jo-1 positive patients were found to have antibodies in their sera that bound the rHRS antigen. When the same type of ELISA was performed on eight anti-Jo-1 negative myositis patients, three patients with SLE or other autoimmune diseases, and three normal controls, no binding affinity greater than that observed in the control wild type baculoviral proteins was found. This indicated that the rHRS protein was as specific as the purified HeLa cell HRS and could be used to test for autoimmune diseases in humans.

In additional experiments, we discovered that the rHRS not only had more binding affinity for anti-Jo-1 antibodies, but was also more stable than purified HRS.

Stability of rHRS

HRS purified from HeLa cells is only stable for a few hours after isolation (Biswas et al. *Federation of European Biochemical Societies* (1988) 229(1): 203–205). This instability presents problems in developing an efficient assay since fresh HRS isolations were necessary for every ELISA. For this reason, it would provide a tremendous advantage to have a protein with similar antigenic sites as HRS, but having an increased stability. Unexpectedly, we discovered that the recombinant HRS is much more stable than HeLa cell purified HRS.

The following ELISAs illustrate the increased stability of rHRS in comparison to purified HRS. Immulon 1® microtiter plates were used in the experiment. Recombinant HRS was first diluted as described in Tables 2 and 3 with PBS. 50λ/well of diluted rHRS was incubated for 2 hours at room temperature. The wells were aspirated and 100λ/well of PBS-BSA (10 mg/ml) was added, then incubated for 4 hours at room temperature. The wells were washed again with PBS-tween three times, followed by two rinses with $H_2O$. 50λ/well of the TEST SERUM 97 (from a polymyositis patient) diluted by the indicated factors in PBS-BSA was added to each well and incubated for 2 hours at room temperature. After incubation, the wells were washed three times with PBS-tween and twice with $H_2O$. 50 λ of goat anti-human-Ig (conjugated to Alkaline Phosphatase) was diluted 1:2000 in PBS-BSA and added to each well for 2 hours at room temperature. The wells were again washed three times in PBS-tween and twice in $H_2O$. 100λ substrate (4-nitrophenyl phosphate BM 726923) was diluted as directed by the manufacturer and added to each well. The $OD_{405}$ of each well was then read in a microtiter plate reader.

In the first part of the experiment, freshly prepared rHRS was the antigen (Table 2). In the second part of this experiment, rHRS was stored as a cytoplasmic extract of baculovirus-infected cells for 2 weeks at −80° C. (Table 3). In the third part of this experiment, rHRS was stored after being bound to the microtiter plate at −80° C. for two weeks (Table 4). As illustrated by the similar results in Tables 2–4, there was very little degradation in the binding affinity of anti-Jo-1 serum to the rHRS after storage for two weeks at −80° C.

Furthermore, plates stored an additional two weeks at −20° C. or at +4° C. showed very little reduction in sensitivity for detecting anti-Jo-1 antibodies from a positive serum. Amazingly, ELISAs performed on rHRS stored for two months at +4° C. had lost no further sensitivity to binding with positive sera. We anticipate that rHRS will be similarly stable at room temperature (+25° C.). These results differ dramatically from similarly performed experiments wherein HRS isolated from HeLa cells was stored at −80° C. After storage for less than 72 hours the amount of enzymatic activity in the HeLa cell isolates was substantially reduced (Biswas et al. *Federation of European Biochemical Societies* (1988) 229 (1): 203–205).

For these reasons, the recombinant HRS provides a much better protein for assays to detect autoimmune diseases. It can be appreciated that other methods known to those of skill in the art could also be used with the rHRS produced in baculovirus to determine binding to anti-Jo-1 antibodies. These methods, for instance, could include a radioimmune assay (RIA), Western Blot or any other method of determining antibody/antigen binding known to those of skill in the art. From this invention it is now possible to make the ELISA plates well in advance of performing the experiment. This provides a tremendous commercial advantage over previous ELISAs that had unstable purified HeLa cell HRS.

TABLE 2

TEST SERUM 97
Not Stored Prior to ELISA

| Antibody Dilution | Antigen Dilution | | | | | |
|---|---|---|---|---|---|---|
| | 1:500 | 1:1000 | 1:2000 | 1:4000 | 1:8000 | 1:16000 |
| 1:1000 | 0.429 | 0.415 | 0.308 | 0.129 | 0.113 | 0.077 |

TABLE 2-continued

TEST SERUM 97
Not Stored Prior to ELISA

| | | | | | |
|---|---|---|---|---|---|
| 1:2000 | 0.429 | 0.270 | 0.308 | 0.123 | 0.069 | 0.065 |
| 1:4000 | 0.354 | 0.351 | 0.213 | 0.104 | 0.075 | 0.064 |
| 1:8000 | 0.278 | 0.236 | 0.248 | 0.086 | 0.069 | 0.064 |
| 1:16000 | 0.196 | 0.161 | 0.132 | 0.090 | 0.067 | 0.062 |
| 1:32000 | 0.136 | 0.178 | 0.155 | 0.104 | 0.070 | 0.060 |
| 1:64000 | 0.139 | 0.104 | 0.088 | 0.071 | 0.062 | 0.060 |

Controls

| Ag | AG + NS | NS | 97 TS | 686 TS | PBS |
|---|---|---|---|---|---|
| 0.066 | 0.076 | 0.059 | 0.059 | 0.061 | 0.060 |

Ag = rHRS, NS = normal serum, 97 TS = serum from polymyositis patient, 686 TS also is serum from polymyositis patient, PBS = Phosphate-buffered saline.

TABLE 3

TEST SERUM 97
Stored for 2 weeks at −80° C.

| Antibody Dilution | Antigen Dilution | | | | | |
|---|---|---|---|---|---|---|
| | 1:500 | 1:1000 | 1:2000 | 1:4000 | 1:8000 | 1:16000 |
| 1:1000 | 0.427 | 0.335 | 0.177 | 0.100 | 0.083 | 0.071 |
| 1:2000 | 0.640 | 0.298 | 0.165 | 0.095 | 0.063 | 0.061 |
| 1:4000 | 0.589 | 0.249 | 0.139 | 0.075 | 0.064 | 0.062 |
| 1:8000 | 0.139 | 0.126 | 0.085 | 0.071 | 0.070 | 0.062 |
| 1:16000 | 0.283 | 0.177 | 0.111 | 0.072 | 0.063 | 0.063 |
| 1:32000 | 0.170 | 0.124 | 0.094 | 0.070 | 0.067 | 0.066 |
| 1:64000 | 0.173 | 0.104 | 0.076 | 0.064 | 0.062 | 0.059 |

Controls

| Ag | AG + NS | NS | 97 TS | 686 TS | PBS |
|---|---|---|---|---|---|
| 0.068 | 0.075 | 0.060 | 0.063 | 0.063 | 0.061 |

Ag = rHRS = Mixture of Antigen and rHRs, NS = normal serum, 97 TS = serum from polymyosins patient, 686 TS also is serum from polymyositis patient, PBS = Phosphate-buffered saline

TABLE 4

TEST SERUM 97
Stored for 2 weeks on microtiter plates at −80° C.

| Antibody Dilution | Antigen Dilution | | | | | |
|---|---|---|---|---|---|---|
| | 1:500 | 1:1000 | 1:2000 | 1:4000 | 1:8000 | 1:16000 |
| 1:1000 | 0.451 | 0.410 | 0.279 | 0.151 | 0.123 | 0.080 |
| 1:2000 | 0.421 | 0.325 | 0.265 | 0.119 | 0.107 | 0.080 |
| 1:4000 | 0.386 | 0.314 | 0.210 | 0.131 | 0.092 | 0.072 |
| 1:8000 | 0.311 | 0.228 | 0.240 | 0.118 | 0.084 | 0.076 |
| 1:16000 | 0.249 | 0.252 | 0.205 | 0.122 | 0.076 | 0.079 |
| 1:32000 | 0.213 | 0.147 | 0.135 | 0.092 | 0.071 | 0.064 |
| 1:64000 | 0.130 | 0.108 | 0.093 | 0.089 | 0.071 | 0.063 |

Controls

| Ag | AG + NS | NS | 97 TS | 686 TS | PBS |
|---|---|---|---|---|---|
| 0.069 | 0.086 | 0.064 | 0.067 | 0.064 | 0.063 |

Ag = rHRS = Mixture of Antigen and rHRs, NS = normal serum, 97 TS = serum from polymyositis patient, 686 TS also is serum from polymyositis patient, PBS = Phosphate-buffered saline After performing the above experiments that demonstrated the increased stability of the rHRS protein, we conducted experiments to determine which fragments of the rHRS peptide were antigenically active.

Determination of Antigenic Fragments of rHRS

Fragments of the rHRS protein were produced by protein synthesis in an Applied Biosystems protein synthesizer by well known methods. Five peptide fragments were used in competitive inhibitory assays to determine their ability to block anti-Jo-1 serum binding to rHRS on ELISA plates. The following five fragments of rHRS were prepared:

| Fragment Number | Amino Acids |
|---|---|
| 1 | 1–30 |
| 2 | 14–45 |
| 3 | 31–60 |
| 4 | 1–60 |
| 5 | 1–47 |

Samples containing 0.25–500 ng of each protein fragment and anti-Jo-1 serum were incubated at room temperature and then added to wells previously coated with rHRS. Positive binding between the anti-Jo-1 serum and the plate-bound rHRS would indicate that the test fragment was unable to bind the anti-Jo-1 antibodies. Negative binding between the anti-Jo-1 serum and the plate-bound rHRS would indicate that the test fragment was able to bind the anti-Jo-1 antibodies and competitively inhibit the ELISA.

In this experiment, Peptide fragments 4 (amino acids 160) and 5 (amino acids 1–47) were able to block the interaction of anti-Jo-1 positive serum with recombinant HRS at fragment concentrations of 250–500 ng/well. In control experiments, a complete length rHRS peptide was, as expected, able to block binding. Amino acid fragments 1, 2 and 3 were unable to detectably block anti-Jo-1 binding in this assay up to a concentration of 500 ng/well.

As an extension of the previously discussed method, we bound the five peptide fragments onto ELISA plates to directly test their binding to anti-Jo-1 positive serum. Peptides 1–5 were placed in wells at 2.5–25,000 ng/well and blocked with 10 mg/ml BSA. Antiserum 97 (anti-Jo-1 positive) was added followed by standard-ELISA protocols. As expected from the previous data Fragments 1 and 2 were negative. Fragment 3 was weakly positive, while Fragments 4 and 5 were strongly positive. We have therefore determined that amino acid rHRS Fragments 3, 4 or 5 can be used as antigens in an ELISA assay to detect anti-Jo-1 positive serum. ELISAs using these antigenic fragments therefore present a way of detecting the presence of an autoimmune disease in a human. It can be appreciated that other methods known to those of skill in the art could also be used with the inventive peptide fragments to determine binding to anti-Jo-1 antibodies. These methods, for instance, could include a radioimmune assay (RIA), Western Blot or any other method of determining antibody/antigen binding known to those of skill in the art.

It is also anticipated that kits can be developed to detect binding of autoimmune antibodies with rHRS produced in non-mammalian host cells. These kits contain, for instance, recombinant Histidyl tRNA synthetase, a vessel for performing the binding assay, and reagents for detecting binding of rHRS to the autoimmune antibodies. Vessels could be microtiter plates, tubes, bottles, or any other container for performing a binding assay. The reagents for detecting binding could be, for example, ELISA reagents such as labeled goat anti-human antibodies, along with the proper buffers for performing an ELISA assay. ELISAs are well known methods by those with skill in the art. A large number of other sets of reagents are known for use in the large number of suitable immunoassays known to those having ordinary skill in the art. The appropriate regents for each of these immunoassays can be readily ascertained by those having ordinary skill in the art For example, "Immunochemical Assays and Biosensor Technology for the 1990's") Nakamura et al (eds), American Society for Microbiology (1992), the disclosure of which is hereby incorporated by reference, lists a large number of isotopic and nonisotopic immunoassays that can be adapted for detection of HRS antigen within the scope of the present invention. The reagents necessary for any particular immunoassay can be readily determined by those having ordinary skill in the art. Generally, these reagents will include a label, such as a radionuclide, enzyme, fluorescent label, luminescent label, vesicle label or particle label. Appropriate additional reagents for detection of the label are required for detection of some of these labels, such as a substrate for an enzyme label or an agglutination product, such as erythrocytes, latex or gelatin, for particle labels.

It can be appreciated that the scope of the present invention should not be limited by the previous examples, but is defined by the following claims.

We claim:

1. A method for determining the presence of an autoimmune disease in a mammal comprising:

isolating a sample of body fluid from a mammal, said body fluid containing antibodies;

contacting said isolated body fluid with recombinant Histidyl tRNA synthetase produced by expression of a mammalian Histidyl tRNA synthetase transfected into host insect cells, said recombinant Histidyl tRNA synthetase being substantially free of endogenous mammalian Histidyl tRNA synthetase immunoreactivity produced by said cells; and detecting the presence or absence of binding of said antibodies to said recombinant Histidyl tRNA synthetase, wherein detectable binding of said antibodies to said recombinant Histidyl tRNA synthetase indicates the presence of an autoimmune disease in said mammal.

2. The method of claim 1, wherein said body fluid is blood serum.

3. The method of claim 1, wherein said autoimmune disease is selected from the group consisting of myositis, polymyositis and dermatomyositis.

4. The-method of claim 1, wherein prior to said contacting step, said recombinant Histidyl tRNA synthetase is stored for greater than 24 hours.

5. The method of claim 1, wherein said contacting and detecting steps comprises an enzyme-linked immunosorbent assay (ELISA).

6. The method of claim 4, wherein said Histidyl tRNA is stored at a temperature within the range −80° C. to 25° C.

7. A kit for determining the presence of antibodies from an autoimmune disease in the blood serum of a mammal comprising:

recombinant histidyl tRNA synthetase produced by expression of an oligonucleotide coding for mammalian histidyl tRNA synthetase transfected into host insect cells, wherein said recombinant histidyl tRNA synthetase is substantially free from endogenous mammalian histidyl tRNA synthetase immunoreactivity produced by said host cells;

a vessel for performing an assay to detect binding of said antibodies to said recombinant Histidyl tRNA synthetase;

reagents for detecting the binding of said antibodies to said recombinant Histidyl tRNA synthetase, wherein positive binding indicates the presence of an autoimmune disease in said mammal.

8. The kit of claim 7, wherein said vessel is a microtiter plate.

9. The kit of claim 7, wherein said reagents for detecting the binding of said antibodies to said recombinant Histidyl tRNA synthetase comprise labeled anti-human antibodies.

10. The kit of claim 7, wherein said reagents for detecting comprise reagents for performing an ELISA.

* * * * *

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:1:

GGCTGGGGCA ACCACCGCAG 20

( 2 ) INFORMATION FOR SEQ ID NO:2:

( i ) SEQUENCE CHARACTERISTICS:
        ( A ) LENGTH: 21
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:2:

TCTCCTTTGA CCTGAGCCTT G 21

( 2 ) INFORMATION FOR SEQ ID NO:3:

( i ) SEQUENCE CHARACTERISTICS:
        ( A ) LENGTH: 25
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:3:

AGAATGAGAT GGTGGGAGAG AAGGG 25

( 2 ) INFORMATION FOR SEQ ID NO:4:

( i ) SEQUENCE CHARACTERISTICS:
    ( A ) LENGTH: 24
    ( B ) TYPE: nucleic acid
    ( C ) STRANDEDNESS: double
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:4:

GCCTGAAGAT CATGTGCGAG ATCC      24

( 2 ) INFORMATION FOR SEQ ID NO:5:

( i ) SEQUENCE CHARACTERISTICS:
    ( A ) LENGTH: 23
    ( B ) TYPE: nucleic acid
    ( C ) STRANDEDNESS: double
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:5:

TTGCACCTGA GGTGGCTGAC CGC      23

( 2 ) INFORMATION FOR SEQ ID NO:6:

( i ) SEQUENCE CHARACTERISTICS:
    ( A ) LENGTH: 23
    ( B ) TYPE: nucleic acid
    ( C ) STRANDEDNESS: double
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:6:

TTGCACCAGA AGTGGCTGAT CGC      23

( 2 ) INFORMATION FOR SEQ ID NO:7:

( i ) SEQUENCE CHARACTERISTICS:
    ( A ) LENGTH: 20
    ( B ) TYPE: nucleic acid
    ( C ) STRANDEDNESS: double
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:7:

GCAGAGCGTG CGGCGCTGGA      20

( 2 ) INFORMATION FOR SEQ ID NO:8:

( i ) SEQUENCE CHARACTERISTICS:
    ( A ) LENGTH: 21

( B ) TYPE: nucleic acid
            ( C ) STRANDEDNESS: double
            ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:8:

TGCGTGGGGA GACATCCGGG G                                    21

( 2 ) INFORMATION FOR SEQ ID NO:9:

( i ) SEQUENCE CHARACTERISTICS:
            ( A ) LENGTH: 22
            ( B ) TYPE: nucleic acid
            ( C ) STRANDEDNESS: double
            ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:9:

GAGGCTCTCT AGGCGTGCGA GC                                   22

( 2 ) INFORMATION FOR SEQ ID NO:10:

( i ) SEQUENCE CHARACTERISTICS:
            ( A ) LENGTH: 25
            ( B ) TYPE: nucleic acid
            ( C ) STRANDEDNESS: double
            ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:10:

CAGACTGGAC TAAGCCTCCT GGGCC                                25

( 2 ) INFORMATION FOR SEQ ID NO:11:

( i ) SEQUENCE CHARACTERISTICS:
            ( A ) LENGTH: 22
            ( B ) TYPE: nucleic acid
            ( C ) STRANDEDNESS: double
            ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:11:

TGGGTTCTTC TTGTACAGCA GG                                   22

( 2 ) INFORMATION FOR SEQ ID NO:12:

( i ) SEQUENCE CHARACTERISTICS:
            ( A ) LENGTH: 23
            ( B ) TYPE: nucleic acid
            ( C ) STRANDEDNESS: double
            ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:12:

AGTCTCTGTT CCACGATGGA GAA 23

( 2 ) INFORMATION FOR SEQ ID NO:13:

( i ) SEQUENCE CHARACTERISTICS:
        ( A ) LENGTH: 24
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:13:

CCACCATGGT TGCTGGACAT AGTC 24

( 2 ) INFORMATION FOR SEQ ID NO:14:

( i ) SEQUENCE CHARACTERISTICS:
        ( A ) LENGTH: 23
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:14:

ACACTGCCCA CACCCAGGGG CTC 23

( 2 ) INFORMATION FOR SEQ ID NO:15:

( i ) SEQUENCE CHARACTERISTICS:
        ( A ) LENGTH: 23
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:15:

ACACTGCCCA CANCCANGGG CTC 23

( 2 ) INFORMATION FOR SEQ ID NO:16:

( i ) SEQUENCE CHARACTERISTICS:
        ( A ) LENGTH: 21
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:16:

TGTCCAAGCT TGTCTACTGA G　　　　　　　　　　　　　　　　　　21

( 2 ) INFORMATION FOR SEQ ID NO:17:

( i ) SEQUENCE CHARACTERISTICS:
    ( A ) LENGTH: 20
    ( B ) TYPE: nucleic acid
    ( C ) STRANDEDNESS: double
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:17:

TATCCAGCTT GTCTACTGAG　　　　　　　　　　　　　　　　　　　20

( 2 ) INFORMATION FOR SEQ ID NO:18:

( i ) SEQUENCE CHARACTERISTICS:
    ( A ) LENGTH: 23
    ( B ) TYPE: nucleic acid
    ( C ) STRANDEDNESS: double
    ( D ) TOPOLOGY: linear ( i ) MOLECULE TYPE: cDNA ( i i i ) HYPOTHETICAL: NO ( i v ) ANTI-SENSE: NO ( x i ) SEQUENCE DESCRIPTION: SEQ ID NO:18:

CTTGGGGGTT TTGAGCACAA ATT　　　　　　　　　　　　　　　　23

( 2 ) INFORMATION FOR SEQ ID NO:19:

( i ) SEQUENCE CHARACTERISTICS:
    ( A ) LENGTH: 22
    ( B ) TYPE: nucleic acid
    ( C ) STRANDEDNESS: double
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:19:

CCACTTGAGC CGCCTGCTGT CT　　　　　　　　　　　　　　　　　22

( 2 ) INFORMATION FOR SEQ ID NO:20:

( i ) SEQUENCE CHARACTERISTICS:
    ( A ) LENGTH: 20
    ( B ) TYPE: nucleic acid
    ( C ) STRANDEDNESS: double
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:20:

GGCTACTAAG GGAACTTGGG 20

( 2 ) INFORMATION FOR SEQ ID NO:21:

( i ) SEQUENCE CHARACTERISTICS:
        ( A ) LENGTH: 491 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i i ) IMMEDIATE SOURCE:
        ( B ) CLONE: Eco ( x i ) SEQUENCE DESCRIPTION: SEQ ID NO:21:

| Ala | Lys | Asn | Ile | Gln | Ala | Ile | Arg | Gly | Met | Asn | Asp | Tyr | Leu | Pro | Gly |
|---|---|---|---|---|---|---|---|---|---|---|---|---|---|---|---|
| 1 | | | | 5 | | | | | 10 | | | | | 15 | |
| Glu | Thr | Ala | Ile | Trp | Gln | Arg | Ile | Glu | Gly | Thr | Leu | Lys | Asn | Val | Leu |
| | | | 20 | | | | | 25 | | | | | 30 | | |
| Gly | Ser | Tyr | Gly | Tyr | Ser | Glu | Ile | Arg | Leu | Pro | Ile | Val | Glu | Gln | Thr |
| | | 35 | | | | | 40 | | | | | 45 | | | |
| Pro | Leu | Phe | Lys | Arg | Ala | Ile | Gly | Glu | Val | Thr | Asp | Val | Val | Glu | Lys |
| | 50 | | | | | 55 | | | | | 60 | | | | |
| Glu | Met | Tyr | Thr | Phe | Glu | Asp | Arg | Asn | Gly | Asp | Ser | Leu | Thr | Leu | Arg |
| 65 | | | | 70 | | | | | 75 | | | | | 80 | |
| Pro | Glu | Gly | Thr | Ala | Gly | Cys | Val | Arg | Ala | Gly | Ile | Glu | His | Gly | Leu |
| | | | | 85 | | | | | 90 | | | | | 95 | |
| Leu | Tyr | Asn | Gln | Glu | Gln | Arg | Leu | Trp | Tyr | Ile | Gly | Pro | Met | Phe | Arg |
| | | | 100 | | | | | 105 | | | | | 110 | | |
| His | Glu | Arg | Pro | Gln | Xaa | Xaa | Lys | Gly | Arg | Tyr | Arg | Gln | Phe | His | Gln |
| | | 115 | | | | | 120 | | | | | 125 | | | |
| Leu | Gly | Cys | Glu | Val | Phe | Gly | Leu | Gln | Gly | Pro | Asp | Ile | Xaa | Asp | Ala |
| | 130 | | | | | 135 | | | | | 140 | | | | |
| Glu | Leu | Ile | Met | Leu | Thr | Ala | Arg | Trp | Trp | Arg | Ala | Leu | Gly | Ile | Ser |
| 145 | | | | | 150 | | | | | 155 | | | | | 160 |
| Glu | Xaa | His | Val | Thr | Leu | Glu | Leu | Asn | Ser | Ile | Xaa | Gly | Ser | Leu | Glu |
| | | | | 165 | | | | | 170 | | | | | 175 | |
| Ala | Arg | Ala | Asn | Tyr | Arg | Asp | Ala | Leu | Val | Ala | Phe | Leu | Glu | Gln | His |
| | | | 180 | | | | | 185 | | | | | 190 | | |
| Lys | Glu | Lys | Leu | Asp | Xaa | Xaa | Xaa | Xaa | Glu | Asp | Cys | Lys | Arg | Arg | Met |
| | | 195 | | | | | 200 | | | | | 205 | | | |
| Tyr | Thr | Asn | Xaa | Xaa | Xaa | Xaa | Xaa | Xaa | Xaa | Pro | Leu | Arg | Val | Xaa | Xaa |
| | 210 | | | | | 215 | | | | | 220 | | | | |
| Xaa | Xaa | Xaa | Leu | Asp | Ser | Lys | Asn | Pro | Glu | Val | Gln | Ala | Leu | Leu | Asn |
| 225 | | | | | 230 | | | | | 235 | | | | | 240 |
| Asp | Ala | Pro | Ala | Leu | Gly | Asp | Tyr | Leu | Asp | Glu | Glu | Ser | Arg | Glu | His |
| | | | | 245 | | | | | 250 | | | | | 255 | |
| Phe | Ala | Gly | Leu | Cys | Lys | Leu | Leu | Glu | Ser | Ala | Gly | Ile | Ala | Tyr | Thr |
| | | | 260 | | | | | 265 | | | | | 270 | | |
| Val | Asn | Gln | Arg | Xaa | Xaa | Xaa | Xaa | Xaa | Xaa | Leu | Val | Arg | Gly | Leu | Asp |

-continued

```
                    275                      280                      285
    Tyr  Tyr  Asn  Arg  Thr  Val  Phe  Glu  Trp  Val  Thr  Asn  Ser  Leu  Gly  Ser
         290                      295                      300

Gln  Xaa  Xaa  Xaa  Xaa  Xaa  Xaa  Xaa  Xaa  Xaa  Xaa  Xaa  Xaa  Xaa  Xaa  Xaa
    305                      310                      315                      320

Xaa  Xaa  Xaa  Xaa  Xaa  Xaa  Xaa  Gly  Thr  Val  Cys  Ala  Gly  Gly  Arg  Tyr
                        325                      330                      335

Asp  Gly  Leu  Val  Glu  Gln  Leu  Gly  Gly  Arg  Ala  Thr  Xaa  Xaa  Xaa  Xaa
                   340                      345                      350

Xaa  Xaa  Pro  Ala  Val  Gly  Phe  Ala  Met  Gly  Leu  Glu  Arg  Leu  Val  Leu
              355                      360                      365

Leu  Val  Gln  Xaa  Xaa  Xaa  Xaa  Ala  Val  Asn  Pro  Glu  Phe  Lys  Ala  Asp
         370                      375                      380

Pro  Val  Val  Asp  Ile  Tyr  Leu  Val  Ala  Ser  Gly  Ala  Asp  Thr  Ser  Gln
    385                      390                      395                      400

Ala  Ala  Met  Ala  Leu  Ala  Glu  Arg  Leu  Arg  Xaa  Xaa  Asp  Glu  Leu  Xaa
                        405                      410                      415

Xaa  Pro  Gly  Val  Lys  Leu  Xaa  Met  Thr  Asn  His  Gly  Gly  Gly  Asn  Phe
                   420                      425                      430

Lys  Lys  Gln  Phe  Ala  Arg  Ala  Asp  Lys  Trp  Gly  Ala  Arg  Val  Ala  Val
                   435                      440                      445

Val  Leu  Gly  Glu  Ser  Glu  Val  Ala  Asn  Gly  Thr  Ala  Val  Val  Lys  Asp
         450                      455                      460

Leu  Xaa  Xaa  Xaa  Xaa  Arg  Ser  Gly  Glu  Gln  Thr  Ala  Val  Ala  Gln  Asp
    465                      470                      475                      480

Ser  Val  Ala  Ala  His  Leu  Arg  Thr  Leu  Leu  Gly
                        485                      490
```

( 2 ) INFORMATION FOR SEQ ID NO:22:

( i ) SEQUENCE CHARACTERISTICS:
        ( A ) LENGTH: 561 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i i ) IMMEDIATE SOURCE:
        ( B ) CLONE: Yea ( x i ) SEQUENCE DESCRIPTION: SEQ ID NO:22:

```
    Met  Ser  Ser  Ala  Thr  Ala  Xaa  Xaa  Xaa  Xaa  Xaa  Xaa  Xaa  Xaa  Xaa  Xaa
    1                   5                        10                       15

Xaa  Xaa  Xaa  Xaa  Xaa  Xaa  Xaa  Xaa  Xaa  Xaa  Ala  Ala  Thr  Ser  Ala  Pro
                        20                       25                       30

Thr  Ala  Asn  Ala  Ala  Asn  Xaa  Xaa  Ala  Leu  Lys  Ala  Ser  Lys  Ala  Pro
                   35                       40                       45

Lys  Lys  Gly  Lys  Leu  Gln  Val  Ser  Leu  Lys  Thr  Pro  Lys  Gly  Thr  Lys
         50                       55                       60

Asp  Trp  Ala  Asp  Ser  Asp  Met  Val  Ile  Arg  Glu  Ala  Ile  Phe  Ser  Thr
    65                       70                       75                       80

Leu  Ser  Gly  Leu  Phe  Lys  Lys  His  Gly  Gly  Val  Thr  Ile  Asp  Thr  Pro
```

-continued

```
                        85                          90                          95
     Val  Phe  Glu  Leu  Arg  Glu  Ile  Leu  Ala  Gly  Lys  Tyr  Gly  Glu  Asp  Ser
                    100                      105                 110

Xaa  Xaa  Xaa  Xaa  Lys  Leu  Ile  Tyr  Asn  Leu  Glu  Asp  Gln  Gly  Gly  Glu
               115                      120                      125

Leu  Cys  Ser  Leu  Arg  Tyr  Asp  Leu  Thr  Val  Pro  Phe  Ala  Arg  Tyr  Val
          130                      135                 140

Ala  Met  Asn  Asn  Ile  Xaa  Xaa  Xaa  Gln  Ser  Ile  Lys  Arg  Tyr  His  Ile
     145                      150                      155                      160

Ala  Lys  Val  Tyr  Arg  Arg  Asp  Gln  Pro  Ala  Met  Thr  Lys  Gly  Arg  Met
                    165                      170                      175

Arg  Glu  Phe  Tyr  Gln  Cys  Asp  Phe  Asp  Val  Ala  Gly  Thr  Phe  Glu  Ser
                    180                      185                      190

Met  Val  Pro  Asp  Ser  Glu  Cys  Leu  Ser  Ile  Leu  Val  Glu  Gly  Leu  Thr
               195                      200                      205

Ser  Leu  Gly  Ile  Lys  Asp  Phe  Lys  Ile  Lys  Leu  Asn  His  Arg  Lys  Ile
          210                      215                      220

Leu  Asp  Gly  Ile  Phe  Gln  Ile  Ala  Gly  Val  Lys  Asp  Glu  Asp  Val  Arg
     225                      230                      235                      240

Lys  Ile  Ser  Ser  Ala  Val  Asp  Lys  Leu  Asp  Lys  Ser  Pro  Trp  Glu  Ala
                    245                      250                      255

Val  Lys  Lys  Glu  Met  Thr  Glu  Glu  Lys  Gly  Gln  Ser  Glu  Glu  Thr  Ala
                    260                      265                      270

Asp  Lys  Ile  Gly  Glu  Tyr  Val  Lys  Leu  Asn  Gly  Ser  Leu  Lys  Glu  Ile
               275                      280                      285

His  Ala  Val  Leu  Ser  Ala  Asp  Ala  Asn  Ile  Thr  Ser  Xaa  Xaa  Asn  Glu
          290                      295                      300

Lys  Ala  Lys  Gln  Gly  Leu  Asp  Asp  Ile  Xaa  Ala  Thr  Leu  Met  Lys  Tyr
     305                      310                      315                      320

Thr  Glu  Ala  Phe  Asp  Ile  Asp  Ser  Phe  Ile  Ser  Phe  Asp  Leu  Ser  Leu
                    325                      330                      335

Ala  Arg  Gly  Leu  Asp  Tyr  Tyr  Thr  Gly  Leu  Ile  Tyr  Glu  Val  Val  Thr
                    340                      345                      350

Ser  Ala  Ser  Ala  Pro  Pro  Glu  Asn  Ala  Ser  Glu  Leu  Lys  Lys  Lys  Ala
               355                      360                      365

Lys  Ser  Ala  Glu  Asp  Ala  Ser  Glu  Phe  Val  Gly  Val  Gly  Ser  Ile  Ala
          370                      375                      380

Ala  Gly  Gly  Arg  Tyr  Asp  Asn  Leu  Val  Asn  Met  Phe  Ser  Glu  Ala  Ser
     385                      390                      395                      400

Gly  Lys  Lys  Ser  Thr  Gln  Ile  Pro  Cys  Val  Gly  Ile  Ser  Phe  Gly  Val
                    405                      410                      415

Glu  Arg  Ile  Phe  Ser  Leu  Ile  Lys  Gln  Arg  Ile  Asn  Ser  Xaa  Ser  Thr
                    420                      425                      430

Thr  Ile  Lys  Pro  Thr  Ala  Thr  Xaa  Gln  Val  Phe  Val  Met  Ala  Phe  Gly
               435                      440                      445

Gly  Gly  Lys  Asp  Trp  Thr  Gly  Tyr  Xaa  Leu  Pro  Glu  Arg  Met  Lys  Val
          450                      455                      460

Thr  Lys  Gln  Leu  Trp  Asp  Ala  Gly  Ile  Glu  Ala  Glu  Tyr  Val  Tyr  Lys
     465                      470                      475                      480

Ala  Lys  Ala  Asn  Pro  Arg  Lys  Gln  Phe  Asp  Thr  Thr  Lys  Lys  Ala  Gly
                    485                      490                      495

Cys  His  Ile  Ala  Val  Ile  Leu  Gly  Lys  Glu  Glu  Tyr  Leu  Glu  Gly  Lys
                    500                      505                      510
```

|           |           |           |           |           |           |           |           |           |           |           |           |           |           |           |           |
|-----------|-----------|-----------|-----------|-----------|-----------|-----------|-----------|-----------|-----------|-----------|-----------|-----------|-----------|-----------|-----------|
| Leu | Arg | Val<br>515 | Lys | Arg | Leu | Gly | Gln<br>520 | Glu | Phe | Ala | Asp | Asp<br>525 | Asp | Gly | Glu |
| Leu | Val<br>530 | Ser | Ala | Ala | Asp | Ile<br>535 | Val | Pro | Ile | Val | Gln<br>540 | Glu | Lys | Leu | Ser |
| Gln<br>545 | Ile | His | Glu | Asp | Gly<br>550 | Leu | Asn | Glu | Val | Thr<br>555 | Arg | Leu | Ile | Lys | Gly<br>560 |
| Leu |

( 2 ) INFORMATION FOR SEQ ID NO:23:

( i ) SEQUENCE CHARACTERISTICS:
        ( A ) LENGTH: 560 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i i ) IMMEDIATE SOURCE:
        ( B ) CLONE: Hum ( x i ) SEQUENCE DESCRIPTION: SEQ ID NO:23:

|           |           |           |           |           |           |           |           |           |           |           |           |           |           |           |           |
|-----------|-----------|-----------|-----------|-----------|-----------|-----------|-----------|-----------|-----------|-----------|-----------|-----------|-----------|-----------|-----------|
| Met<br>1 | Ala | Glu | Arg | Ala<br>5 | Ala | Leu | Glu | Glu | Leu<br>10 | Val | Lys | Leu | Gln | Gly<br>15 | Glu |
| Arg | Xaa | Val | Arg<br>20 | Gly | Leu | Lys | Gln | Gln<br>25 | Lys | Ala | Ser | Ala | Glu<br>30 | Leu | Ile |
| Glu | Glu | Glu<br>35 | Val | Ala | Lys | Leu | Leu<br>40 | Lys | Leu | Lys | Ala | Gln<br>45 | Leu | Gly | Pro |
| Asp | Glu<br>50 | Ser | Lys | Gln | Lys | Phe<br>55 | Val | Leu | Lys | Thr | Pro<br>60 | Lys | Gly | Thr | Arg |
| Asp<br>65 | Tyr | Ser | Pro | Arg | Gln<br>70 | Met | Ala | Val | Arg | Glu<br>75 | Lys | Val | Phe | Asp | Val<br>80 |
| Ile | Ile | Arg | Cys | Phe<br>85 | Lys | Arg | His | Gly | Ala<br>90 | Glu | Val | Ile | Asp | Thr<br>95 | Pro |
| Val | Phe | Glu | Leu<br>100 | Lys | Glu | Thr | Leu | Met<br>105 | Gly | Lys | Tyr | Gly | Glu<br>110 | Asp | Ser |
| Xaa | Xaa | Xaa<br>115 | Xaa | Lys | Leu | Ile | Tyr<br>120 | Asp | Leu | Lys | Asp | Gln<br>125 | Gly | Gly | Glu |
| Leu | Leu<br>130 | Ser | Leu | Arg | Tyr | Asp<br>135 | Leu | Thr | Val | Pro | Phe<br>140 | Ala | Arg | Tyr | Leu |
| Ala<br>145 | Met | Asn | Lys | Leu | Xaa<br>150 | Xaa | Xaa | Thr | Asn | Ile<br>155 | Lys | Arg | Tyr | His | Ile<br>160 |
| Ala | Lys | Val | Tyr | Arg<br>165 | Arg | Asp | Asn | Pro | Ala<br>170 | Met | Thr | Arg | Gly | Arg<br>175 | Tyr |
| Arg | Glu | Phe | Tyr<br>180 | Gln | Cys | Asp | Phe | Asp<br>185 | Ile | Ala | Gly | Asn | Phe<br>190 | Asp | Pro |
| Met | Ile | Pro<br>195 | Asp | Ala | Glu | Cys | Leu<br>200 | Lys | Ile | Met | Glu | Ile<br>205 | Leu | Ser | Ser |
| Leu | Gln<br>210 | Ile | Gly | Asp | Phe | Leu<br>215 | Val | Lys | Val | Asn | Asp<br>220 | Arg | Arg | Ile | Leu |
| Asp<br>225 | Gly | Met | Phe | Ala | Ile<br>230 | Cys | Gly | Val | Ser | Asp<br>235 | Ser | Lys | Phe | Arg | Thr<br>240 |

```
Ile Cys Ser Ser Val Asp Lys Leu Asp Lys Val Ser Trp Glu Glu Val
                245                 250                 255

Lys Asn Glu Met Val Gly Glu Lys Gly Leu Ala Pro Glu Val Ala Asp
                260                 265                 270

Arg Ile Gly Asp Tyr Val Gln Gln His Gly Gly Val Ser Leu Val Glu
                275                 280                 285

Gln Leu Leu Xaa Gln Asp Pro Lys Leu Ser Gln Xaa Xaa Asn Lys Gln
        290                 295                 300

Ala Leu Glu Gly Leu Gly Asp Leu Xaa Lys Leu Leu Phe Glu Tyr Leu
305                 310                 315                 320

Thr Leu Phe Gly Ile Asp Asp Lys Ile Ser Phe Asp Leu Ser Leu Ala
                325                 330                 335

Arg Gly Leu Asp Tyr Tyr Thr Gly Val Ile Tyr Glu Ala Val Leu Xaa
                340                 345                 350

Xaa Xaa Xaa Xaa Xaa Xaa Xaa Xaa Xaa Xaa Leu Gln Thr Pro Ala Gln
                355                 360                 365

Ala Gly Glu Glu Pro Leu Xaa Xaa Xaa Gly Val Gly Ser Val Ala Ala
    370                 375                 380

Gly Gly Arg Tyr Asp Gly Leu Val Gly Met Phe Xaa Asp Pro Lys Gly
385                 390                 395                 400

Arg Lys Xaa Xaa Xaa Val Pro Cys Val Gly Leu Ser Ile Gly Val Glu
                405                 410                 415

Arg Ile Phe Ser Ile Val Glu Gln Arg Leu Glu Ala Leu Glu Glu Lys
                420                 425                 430

Ile Arg Thr Thr Glu Thr Xaa Gln Val Leu Val Ala Ser Xaa Xaa Ala
            435                 440                 445

Gln Lys Lys Leu Leu Glu Xaa Xaa Xaa Xaa Glu Arg Leu Lys Leu Val
    450                 455                 460

Ser Glu Leu Trp Asp Ala Gly Ile Lys Ala Glu Leu Leu Tyr Lys Lys
465                 470                 475                 480

Asn Pro Lys Leu Leu Asn Gln Leu Gln Tyr Cys Glu Glu Ala Gly Ile
                485                 490                 495

Pro Leu Val Ala Ile Ile Gly Glu Gln Glu Leu Lys Asp Gly Val Ile
            500                 505                 510

Lys Leu Arg Ser Xaa Xaa Xaa Xaa Xaa Xaa Xaa Xaa Xaa Xaa Xaa Xaa
        515                 520                 525

Val Thr Ser Arg Glu Glu Val Asp Val Arg Arg Glu Asp Leu Xaa Xaa
    530                 535                 540

Val Glu Glu Ile Lys Arg Arg Thr Gly Gln Pro Leu Cys Ile Cys Xaa
545                 550                 555                 560
```

( 2 ) INFORMATION FOR SEQ ID NO:24:

( i ) SEQUENCE CHARACTERISTICS:
        ( A ) LENGTH: 561 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i i ) IMMEDIATE SOURCE:
        ( B ) CLONE: Ham ( x i ) SEQUENCE DESCRIPTION: SEQ ID NO:24:

```
Met  Ala  Ser  Xaa  Pro  Ala  Leu  Glu  Glu  Leu  Val  Leu  Asn  Ser  Arg  His
1                  5                        10                       15

Arg  Leu  Val  Arg  Gly  Leu  Lys  Gln  Gln  Lys  Ala  Ser  Ala  Asp  Gln  Ile
               20                  25                       30

Glu  Glu  Glu  Val  Ala  Lys  Leu  Leu  Lys  Leu  Lys  Ala  Gln  Leu  Gly  His
          35                       40                  45

Asp  Glu  Ser  Lys  Gln  Lys  Phe  Val  Leu  Lys  Thr  Pro  Lys  Gly  Thr  Arg
     50                       55                  60

Asp  Tyr  Ser  Pro  Arg  Gln  Met  Ala  Val  Arg  Glu  Lys  Val  Phe  Asp  Val
65                       70                  75                            80

Ile  Ile  Cys  Cys  Phe  Lys  Arg  His  Gly  Ala  Glu  Val  Ile  Asp  Thr  Pro
               85                       90                       95

Val  Phe  Glu  Leu  Lys  Glu  Thr  Leu  Met  Gly  Lys  Tyr  Gly  Gln  Asp  Cys
               100                      105                      110

Xaa  Xaa  Xaa  Xaa  Lys  Leu  Ile  Tyr  Asp  Leu  Lys  Asp  Gln  Gly  Gly  Glu
          115                      120                      125

Leu  Leu  Ser  Leu  Arg  Tyr  Asp  Leu  Thr  Val  Pro  Phe  Gly  Arg  Tyr  Leu
     130                      135                      140

Ala  Met  Asn  Asn  Leu  Xaa  Xaa  Xaa  Thr  Asn  Ile  Lys  Arg  Tyr  His  Ile
145                      150                      155                      160

Ala  Lys  Val  Tyr  Arg  Arg  Asp  Asn  Pro  Ala  Met  Thr  Arg  Gly  Arg  Tyr
                    165                      170                      175

Leu  Asn  Ser  Ile  Thr  Val  Asp  Phe  Asp  Ile  Ala  Gly  Gln  Phe  Asp  Pro
               180                      185                      190

Met  Ile  Pro  Asp  Ala  Glu  Cys  Leu  Lys  Ile  Met  Cys  Glu  Ile  Leu  Ser
          195                      200                      205

Ser  Leu  Gln  Ile  Gly  Lys  Phe  Leu  Val  Lys  Val  Asn  Asp  Arg  Arg  Ile
     210                      215                      220

Leu  Asp  Gly  Met  Phe  Ala  Val  Cys  Gly  Val  Pro  Asp  Ser  Lys  Phe  Arg
225                      230                      235                      240

Thr  Ile  Cys  Ser  Ser  Val  Asp  Lys  Leu  Asp  Lys  Val  Ser  Trp  Glu  Glu
               245                      250                      255

Val  Lys  Asn  Glu  Met  Val  Gly  Glu  Lys  Gly  Leu  Ala  Pro  Glu  Val  Ala
               260                      265                      270

Asp  Arg  Ile  Gly  Asp  Tyr  Val  Gln  Gln  His  Gly  Glu  Val  Cys  Leu  Val
          275                      280                      285

Glu  Gln  Leu  Leu  Xaa  Gln  Asp  Pro  Lys  Leu  Ser  Gln  Xaa  Xaa  Asn  Lys
     290                      295                      300

Gln  Ala  Val  Glu  Gly  Leu  Gly  Asp  Leu  Xaa  Lys  Leu  Leu  Phe  Glu  Tyr
305                      310                      315                      320

Leu  Thr  Leu  Phe  Gly  Ile  Asp  Asp  Lys  Ile  Ser  Phe  Asp  Leu  Ser  Leu
               325                      330                      335

Ala  Arg  Gly  Leu  Asp  Tyr  Tyr  Thr  Gly  Val  Ile  Tyr  Val  Ala  Val  Leu
               340                      345                      350

Xaa  Xaa  Xaa  Xaa  Xaa  Xaa  Xaa  Xaa  Xaa  Xaa  Xaa  Leu  Gln  Met  Pro  Thr
          355                      360                      365

Gly  Ala  Gly  Glu  Glu  Pro  Trp  Xaa  Xaa  Xaa  Xaa  Cys  Gly  Gln  Cys  Gly
          370                      375                      380

Cys  Trp  Arg  Arg  Tyr  Asp  Gly  Leu  Val  Gly  Met  Phe  Xaa  Asp  Pro  Lys
385                      390                      395                      400

Gly  Arg  Lys  Xaa  Xaa  Xaa  Val  Pro  Cys  Val  Gly  Leu  Ser  Ile  Gly  Val
```

|   |   |   |   |   |   |   |   |   | 405 |   |   |   |   |   | 410 |   |   |   |   |   | 415 |   |
|---|---|---|---|---|---|---|---|---|---|---|---|---|---|---|---|---|---|---|---|---|---|---|

Glu Arg Ile Phe Ser Ile Val Glu Gln Arg Leu Glu Ala Leu Glu Glu
            420                 425             430

Lys Val Arg Thr Thr Glu Thr Xaa Gln Val Leu Val Ala Ser Xaa Xaa
        435                 440                 445

Ala Gln Lys Lys Leu Ala Gly Xaa Xaa Xaa Xaa Gly Glu Thr Lys Ala
    450                 455                 460

Cys Leu Gln Leu Trp Asp Ala Gly Ile Lys Ala Glu Leu Leu Tyr Lys
465                 470                 475                 480

Lys Asn Pro Lys Leu Leu Asn Gln Leu Gln Tyr Cys Glu Glu Thr Gly
            485                 490                 495

Ile Pro Leu Val Ala Ile Ile Gly Glu Gln Glu Leu Lys Asp Gly Val
            500                 505                 510

Ile Lys Leu Arg Ser Xaa Xaa Xaa Xaa Xaa Xaa Xaa Xaa Xaa Xaa Xaa
        515                 520                 525

Xaa Val Ala Ser Arg Glu Glu Val Asp Val Arg Arg Glu Asp Leu Xaa
    530                 535                 540

Xaa Val Glu Glu Ile Arg Arg Arg Thr Asn Gln Pro Leu Tyr Val Cys
545                 550                 555                 560

Xaa